(12) United States Patent
Bokil et al.

(10) Patent No.: US 10,413,737 B2
(45) Date of Patent: Sep. 17, 2019

(54) SYSTEMS AND METHODS FOR PROVIDING THERAPY USING ELECTRICAL STIMULATION TO DISRUPT NEURONAL ACTIVITY

(71) Applicant: Boston Scientific Neuromodulation Corporation, Valencia, CA (US)

(72) Inventors: Hemant Bokil, Santa Monica, CA (US); Stephen Carcieri, Los Angeles, CA (US); Ljubomir Manola, Brusells (BE)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 45 days.

(21) Appl. No.: 15/274,661

(22) Filed: Sep. 23, 2016

(65) Prior Publication Data

US 2017/0087369 A1 Mar. 30, 2017

Related U.S. Application Data

(60) Provisional application No. 62/233,085, filed on Sep. 25, 2015.

(51) Int. Cl.
*A61N 1/372* (2006.01)
*A61N 1/36* (2006.01)
*A61N 1/05* (2006.01)

(52) U.S. Cl.
CPC ....... *A61N 1/37241* (2013.01); *A61N 1/0551* (2013.01); *A61N 1/3615* (2013.01);
(Continued)

(58) Field of Classification Search
CPC ............ A61N 1/36185; A61N 1/36067; A61N 1/36057; A61N 1/37241
(Continued)

(56) References Cited

U.S. PATENT DOCUMENTS 4,602,624 A 7/1986 Naples et al.
4,630,611 A 12/1986 King
(Continued)

FOREIGN PATENT DOCUMENTS

EP 0580928 A1 2/1994
EP 0650694 B1 7/1998
(Continued)

OTHER PUBLICATIONS

Adamchic et al., "Coordinated Reset Neuromodulation for Parkinson's Disease: Proof-of-Concept Study," Movement Disorder, vol. 29, No. 13, 2014, 1679-1684.
(Continued)

*Primary Examiner* — Mallika D Fairchild
*Assistant Examiner* — Minh Duc G Pham
(74) *Attorney, Agent, or Firm* — Lowe Graham Jones PLLC; Bruce E. Black

(57) ABSTRACT

A method for electrical stimulation of a patient includes a) implanting at least a portion of an electrical stimulation lead; b) stimulating the patient using the electrical stimulation lead at multiple test stimulation amplitudes; c) observing a response for each of the test stimulation amplitudes; d) selecting a working stimulation amplitude based on the responses from a group consisting of the test stimulation amplitudes and, optionally, a default stimulation amplitude; e) stimulating the patient using the electrical stimulation lead and the working amplitude at multiple test duty cycles; f) observing a response for each of the test duty cycles; g) selecting a working duty cycle based on the responses from a group consisting of the test duty cycles and, optionally, a default duty cycle; and h) stimulating the patient using the electrical stimulation lead, the working amplitude, and the working duty cycle.

20 Claims, 12 Drawing Sheets

(52) U.S. Cl.
CPC ..... *A61N 1/36067* (2013.01); *A61N 1/36175* (2013.01); *A61N 1/36185* (2013.01)

(58) Field of Classification Search
USPC .......................................................... 607/62
See application file for complete search history.

(56) References Cited

U.S. PATENT DOCUMENTS

| | | |
|---|---|---|
| 4,744,370 A | 5/1988 | Harris |
| 5,000,194 A | 3/1991 | van den Honert et al. |
| 5,070,605 A | 12/1991 | Daglow et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Eisberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,125,302 A | 9/2000 | Kuzma |
| 6,134,478 A | 10/2000 | Spehr |
| 6,161,047 A | 12/2000 | King et al. |
| 6,167,311 A | 12/2000 | Rezai |
| 6,181,969 B1 | 1/2001 | Gord |
| 6,322,559 B1 | 11/2001 | Daulton et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,678,564 B2 | 1/2004 | Ketterl et al. |
| 6,741,892 B1 | 5/2004 | Meadows et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,241,180 B1 | 7/2007 | Rentas |
| 7,244,150 B1 | 7/2007 | Brase et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,489,971 B1 | 2/2009 | Franz |
| 7,668,601 B2 | 2/2010 | Hegland et al. |
| 7,672,734 B2 | 3/2010 | Anderson et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,917,221 B2 | 3/2011 | Tass |
| 7,949,395 B2 | 5/2011 | Kuzma |
| 7,974,698 B2 | 7/2011 | Tass et al. |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,796 B2 | 8/2011 | Tass et al. |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,116,874 B2 | 2/2012 | Tass |
| 8,175,710 B2 | 5/2012 | He |
| 8,224,450 B2 | 7/2012 | Brase |
| 8,225,504 B2 | 7/2012 | Dye et al. |
| 8,271,094 B1 | 9/2012 | Moffitt et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,364,278 B2 | 1/2013 | Pianca et al. |
| 8,391,985 B2 | 3/2013 | McDonald |
| 8,463,378 B2 | 6/2013 | Tass |
| 8,538,547 B2 | 9/2013 | Tass et al. |
| 8,583,237 B2 | 11/2013 | Bedenbaugh |
| 8,688,235 B1 | 4/2014 | Pianca et al. |
| 8,825,167 B2 | 9/2014 | Tass et al. |
| 9,302,069 B2 | 4/2016 | Tass et al. |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0004422 A1* | 1/2006 | De Ridder ........... A61N 1/0529 607/45 |
| 2006/0025841 A1 | 2/2006 | McIntyre |
| 2006/0247697 A1 | 11/2006 | Sharma et al. |
| 2007/0135860 A1 | 6/2007 | Tass |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0030298 A1 | 2/2010 | Martens et al. |
| 2010/0036468 A1 | 2/2010 | Decre et al. |
| 2010/0057176 A1 | 3/2010 | Barker |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0121408 A1* | 5/2010 | Imran ................ A61N 1/36071 607/46 |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0040547 A1* | 2/2011 | Gerber ................ A61N 1/36185 703/11 |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0259386 A1 | 10/2012 | DeRohan et al. |
| 2012/0316615 A1 | 12/2012 | DiGiore et al. |
| 2013/0105071 A1 | 5/2013 | DiGiore et al. |
| 2013/0109254 A1 | 5/2013 | Klardie et al. |

(56) References Cited

U.S. PATENT DOCUMENTS

| | | |
|---|---|---|
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2014/0371810 A1* | 12/2014 | Mokelke ............ A61N 1/36185 607/44 |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |
| 2015/0297444 A1 | 10/2015 | Tass |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0067495 A1* | 3/2016 | Chaturvedi ........ A61N 1/36128 607/59 |
| 2016/0082256 A1 | 3/2016 | Moffitt et al. |
| 2016/0082257 A1 | 3/2016 | Moffitt |
| 2016/0129242 A1 | 5/2016 | Malinowski |
| 2016/0129265 A1 | 5/2016 | Malinowski |
| 2016/0228692 A1 | 8/2016 | Steinke et al. |
| 2016/0296745 A1 | 10/2016 | Govea et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

OTHER PUBLICATIONS

Deuschl et al., "A Randomized Trial of Deep-Brian Stimulation for Parkinson's Disease," The New England Journal of Medicine, 355;9, Aug. 31, 2006, pp. 896-908.

Volkmann et al., "Basic Algorithms for the Programming of Deep Brain Stimulation in Parkinson's Disease," Movement Disorders, vol. 21, Suppl. 14, 2006, pp. S284-S289.

Rosin et al., "Closed-Loop Deep Brain Stimulation Is Superior in Ameliorating Parkinsonism," Neuron 72, Oct. 20, 2011, pp. 370-384.

Little et al., "Adaptive deep brain stimulation for Parkinson's disease demonstrates reduced speech side effects compared to conventional stimulation in the acute setting," J. Nuerol Neurosurg. Psychiatry Month 2016, vol. 0, No. 0, 3 pages.

Tass, "A model of desynchronizing deep brain stimulation with a demand-controlled coordinated reset of neural subpopulations," Biological Cybernetics, 2003, 9 pages.

Tass et al., "Long-term anti-kindling effects of desynchronizing brain stimulation: a theoretical study," Biological Cybernetics, 2006, pp. 58-66.

Hammond et al., "Pathological synchronization in Parkinson's disease: networks, models and treatments," Trends in Neurosciences vol. 30, No. 7, pp. 357-364.

Kuhn et al., "High-Frequency Stimulation of the Subthalamic Nucleus Suppresses Oscillatory B Activity in Patients with Parkinson's Disease in Parallel with Improvement in Motor Performance," The Journal of Neuroscience, Jun. 11, 2008, 28(24), pp. 6165-6173.

Tass et al., "Long-lasting desynchronization in rat hippocampal slice induced by coordinated reset stimulation," Physical Review, E80, 011902, 2009, 4 pages.

Tass et al., "Coordinated Reset Has Sustained Aftereffects in Parkinsonian Monkeys," Annals of Neurology, vol. 72, No. 5, 2012, pp. 816-820.

Temperli et al,. "How do parkinsonian signs return after discontinuation of subthalamic DBS?" Neurology 2003, 60, pp. 78-81.

Meissner et al., "Subthalamic high frequency stimulation resets subthalamic firing and reduces abnormal oscillations," Brain, 2005, 128, pp. 2372-2382.

Unified Parkinson's Disease Rating Scale, PD Workbook—The We Move Clinicians' Guide to Parkinson's Disease, 2006, 8 pages.

Hauptmann et al., "External trial deep brain stimulation device for the application of desynchronizing stimulation techniques," Journal of Neural Engineering 6 (2009), 066003, 13 pages.

Tass et al., "The causal relationship between subcortical local field potential oscillations and Parkinsonian resting tremor," Jornal of Neural Engineering 7 (2010) 016009, 17 pages.

* cited by examiner

SYSTEMS AND METHODS FOR PROVIDING THERAPY USING ELECTRICAL STIMULATION TO DISRUPT NEURONAL ACTIVITY

CROSS-REFERENCE TO RELATED APPLICATIONS

This application claims the benefit under 35 U.S.C. § 119(e) of U.S. Provisional Patent Application Ser. No. 62/233,085, filed Sep. 25, 2015, which is incorporated herein by reference.

FIELD

The present invention is directed to the area of electrical stimulation systems and methods of using the systems. The present invention is also directed to systems and methods for providing therapy using electrical stimulation generated from electrical stimulation systems to disrupt undesired neural activity through desynchronization of action potential propagation along patient tissue.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include an implantable pulse generator (IPG), one or more leads, and an array of stimulator electrodes on each lead. The stimulator electrodes are in contact with or near the nerves, muscles, or other tissue to be stimulated. The pulse generator generates electrical pulses that are delivered by the electrodes to body tissue.

BRIEF SUMMARY

One embodiment is a method for electrical stimulation of a patient that includes a) implanting at least a portion of an electrical stimulation lead including electrodes disposed along a distal end portion of the electrical stimulation lead; b) stimulating the patient using the electrical stimulation lead at multiple test stimulation amplitudes; c) observing a response for each of the test stimulation amplitudes; d) selecting a working stimulation amplitude based on the responses from a group consisting of the test stimulation amplitudes and, optionally, a default stimulation amplitude; e) stimulating the patient using the electrical stimulation lead and the working amplitude at multiple test duty cycles; f) observing a response for each of the test duty cycles; g) selecting a working duty cycle based on the responses from a group consisting of the test duty cycles and, optionally, a default duty cycle; and h) stimulating the patient using the electrical stimulation lead, the working amplitude, and the working duty cycle.

In at least some embodiments, the method further includes i) stimulating the patient using the electrical stimulation lead and the working amplitude and working duty cycle at a plurality of test burst frequencies; j) observing a response for each of the plurality of test burst frequencies; k) selecting a working burst frequency based on the responses from a group consisting of the plurality of test burst frequencies and, optionally, a default burst frequency; and l) stimulating the patient using the electrical stimulation lead, the working amplitude, and the working burst frequency.

In at least some embodiments, the test stimulation amplitudes are predetermined prior to stimulating the patient. In at least some embodiments, stimulating the patient using the electrical stimulation lead at multiple test stimulation amplitudes includes randomly selecting an order of the test stimulation amplitudes. In at least some embodiments, stimulating the patient using the electrical stimulation lead and the working amplitude at multiple test duty cycles includes randomly selecting an order of the test duty cycles.

In at least some embodiments, observing a response for each of the test stimulation amplitudes includes scoring a response for each of the test stimulation amplitudes. In at least some embodiments, observing a response for each of the test duty cycles includes scoring a response for each of the test duty cycles. In at least some embodiments, selecting a working stimulation amplitude includes selecting the default stimulation amplitude if responses for the test stimulation amplitudes fail to meet a threshold criterion.

In at least some embodiments, the method further includes i) after stimulating the patient using the electrical stimulation lead, the working amplitude, and the working duty cycle, observing a response for the stimulation; and j) determining whether the response for the stimulation maintains a threshold level of response. In at least some embodiments, determining whether the response for the stimulation maintains a threshold level of response includes determining whether the response for the stimulation maintains a threshold level of response for each of at least two successive days. In at least some embodiments, steps a) to j) are performed at a hospital or patient care facility and then step i) is repeated at a patient home and then step j) is repeated with a clinician. In at least some embodiments, steps b) to d) are performed on a first day, steps e) to g) are performed over a course of a plurality of second days following the first day, and steps h) to j) are performed over a course of a plurality of third days following the plurality of second days.

In at least some embodiments, the method provides spinal cord stimulation. In at least some embodiments, the method provides deep brain stimulation.

Another embodiment is a system for electrical stimulation of a patient that includes an implantable electrical stimulation lead including a plurality of electrodes disposed along a distal end portion of the electrical stimulation lead; and a computer processor configured and arranged to perform actions. The actions include a) stimulate a patient using the electrical stimulation lead at multiple test stimulation amplitudes; b) receive a response for each of the test stimulation amplitudes; c) select a working stimulation amplitude based on the responses from a group consisting of the test stimulation amplitudes and, optionally, a default stimulation amplitude; d) stimulate the patient using the electrical stimulation lead and the working amplitude at multiple test duty cycles; e) receive a response for each of the test duty cycles; f) select a working duty cycle based on the responses from a group consisting of the test duty cycles and, optionally, a default duty cycle; and g) stimulate the patient using the electrical stimulation lead, the working amplitude, and the working duty cycle.

In at least some embodiments, the actions further include i) stimulating the patient using the electrical stimulation lead and the working amplitude and working duty cycle at a plurality of test burst frequencies; j) observing a response for each of the plurality of test burst frequencies; k) selecting a working burst frequency based on the responses from a group consisting of the plurality of test burst frequencies and, optionally, a default burst frequency; and l) stimulating the patient using the electrical stimulation lead, the working amplitude, and the working burst frequency.

In at least some embodiments, the system further includes a trial stimulator coupleable to the implantable electrical stimulation lead to provide stimulation through the electrical stimulation lead. In at least some embodiments, the system further includes an implantable control module coupleable to the implantable electrical stimulation lead to provide stimulation through the electrical stimulation lead. In at least some embodiments, stimulate the patient using the electrical stimulation lead at a plurality of test stimulation amplitudes includes randomly select an order of the test stimulation amplitudes. In at least some embodiments, stimulate the patient using the electrical stimulation lead at a plurality of test duty cycles includes randomly select an order of the test duty cycles. In at least some embodiments, receive a response for each of the test stimulation amplitudes includes receive a score of a response for each of the test stimulation amplitudes.

In at least some embodiments, the system can be used for spinal cord stimulation. In at least some embodiments, the system can be used for deep brain stimulation.

A further embodiment is a non-transitory computer-readable medium having processor-executable instructions for identifying a set of stimulation parameters, the processor-executable instructions when installed onto a device enable the device to perform actions. The actions include a) stimulate a patient using the electrical stimulation lead at multiple test stimulation amplitudes; b) receive a response for each of the test stimulation amplitudes; c) select a working stimulation amplitude based on the responses from a group consisting of the test stimulation amplitudes and, optionally, a default stimulation amplitude; d) stimulate the patient using the electrical stimulation lead and the working amplitude at multiple test duty cycles; e) receive a response for each of the test duty cycles; f) select a working duty cycle based on the responses from a group consisting of the test duty cycles and, optionally, a default duty cycle; and g) stimulate the patient using the electrical stimulation lead, the working amplitude, and the working duty cycle.

In at least some embodiments, the actions further include i) stimulating the patient using the electrical stimulation lead and the working amplitude and working duty cycle at a plurality of test burst frequencies; j) observing a response for each of the plurality of test burst frequencies; k) selecting a working burst frequency based on the responses from a group consisting of the plurality of test burst frequencies and, optionally, a default burst frequency; and l) stimulating the patient using the electrical stimulation lead, the working amplitude, and the working burst frequency.

In at least some embodiments, receive a response for each of the test stimulation amplitudes includes receive a score of a response for each of the test stimulation amplitudes. In at least some embodiments, receive a response for each of the test duty cycles includes receive a score of a response for each of the test duty cycles.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of electrical stimulation systems and methods of using the systems. The present invention is also directed to systems and methods for providing therapy using electrical stimulation generated from electrical stimulation systems to disrupt undesired neural activity through desynchronization of action potential propagation along patient tissue.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, spinal cord stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

Figure 1:
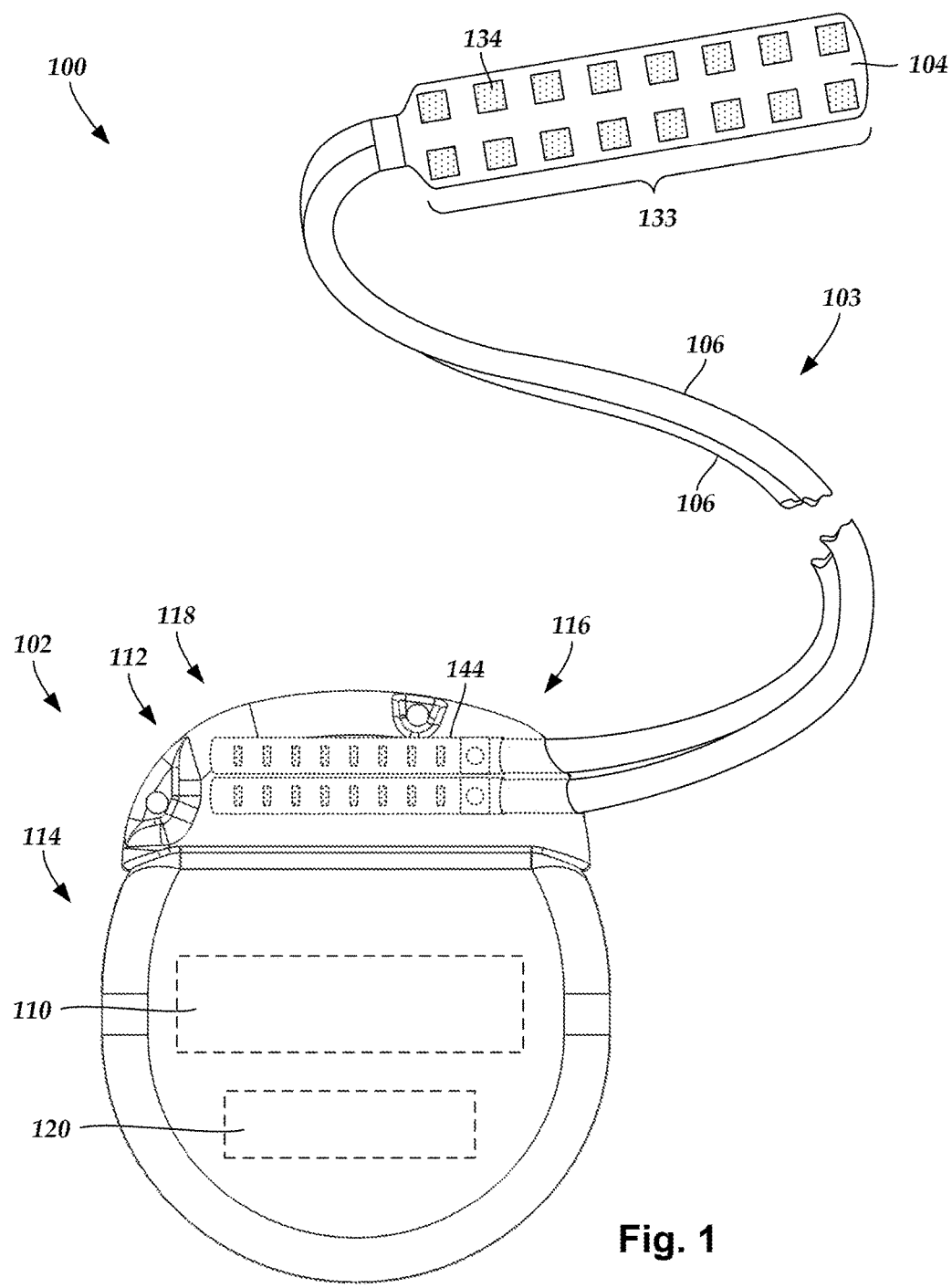
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a device that includes a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 310 in FIG. 3A) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
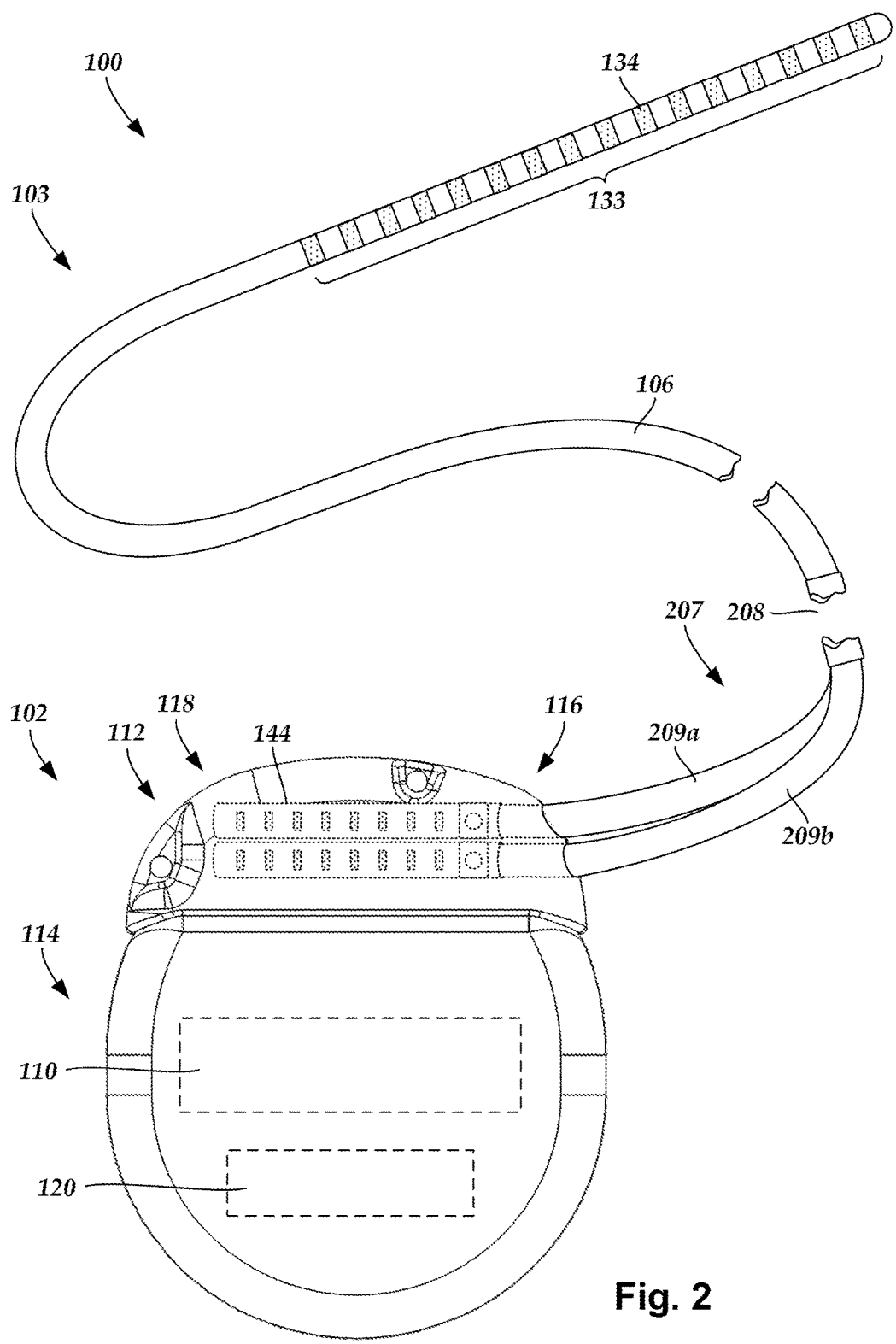
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

Referring to both FIG. 1 and FIG. 2, the lead 103 can be coupled to the control module 102 in any suitable manner. In at least some embodiments, the lead 103 couples directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

Referring to both FIG. 1 and FIG. 2, the control module 102 typically includes a connector housing 112, or "header," and a sealed electronics housing 114. An electronic subassembly 110 and an optional power source 120 are disposed in the sealed electronics housing 114. The connector housing 112 is disposed along a portion of an exterior surface of the sealed electronics housing 114 and includes a first end 116 and an opposing second end 118.

A control-module connector 144 is disposed in the connector housing 112. The control-module connector 144 is configured and arranged to receive, either directly or indirectly, a portion of the lead 103 and make an electrical connection between the lead 103 and the electronic subassembly 110 of the control module 102.

The electrical stimulation system, or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
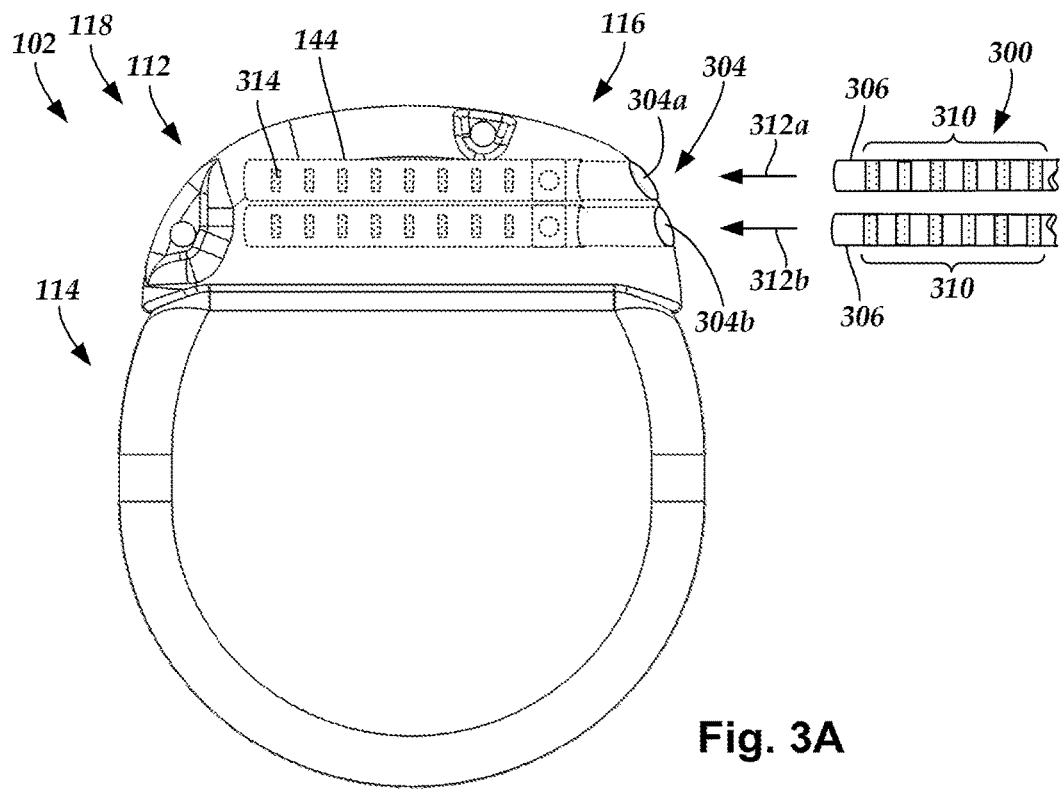
FIG. 3A is a schematic view of one embodiment of the control module of FIG. 1 and two elongated members of a lead assembly, the control module defining two lead-assembly ports configured for receiving the two elongated members of the lead assembly, the control module, according to the invention.

Terminals (e.g., 310 in FIGS. 3A and 3C) are typically disposed along the proximal end portion of the one or more lead bodies 106 of the electrical stimulation system 100 (as well as along proximal end portions of any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3C) which, in turn, are disposed on, for example, the control module 102 (or along a distal end portion of a lead extension, a splitter, an adaptor, or the like). Electrically-conductive wires, cables, or the like ("conductors") (not shown) extend from, in the case of lead bodies, the terminals to the electrodes 134. In the case of intermediate devices (e.g., lead extensions, adaptors, splitters, or the like), the conductors extend from terminals to connector contacts of connectors (see e.g., connector contacts 340 of lead-extension connector 322 of FIG. 3C). Typically, one or more electrodes 134 are electrically coupled to each terminal. In at least some embodiments, each terminal is only connected to one electrode 134.

The conductors may be embedded in the non-conductive material of the lead body 106 (or other elongated members, such as lead extensions, splitters, adaptors, or the like) or can be disposed in one or more lumens (not shown) extending along the lead body 106 (or other elongated member). In some embodiments, there is an individual lumen for each conductor. In other embodiments, two or more conductors extend through a lumen. There may also be one or more stylet lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106 (or other elongated members), for example, for infusion of drugs or medication into the site of implantation. In at least one embodiment, the one or more lumens are flushed continually, or on a regular basis, with saline, epidural fluid, or the like. In at least some embodiments, the one or more lumens are permanently or removably sealable along distal ends of the lumens.

FIG. 3A is a schematic side view of one embodiment of proximal end portions of two elongated members 306 of a lead assembly 300 configured and arranged for coupling to one embodiment of the control-module connector 144. The elongated members 306 of the lead assembly 300 may include, for example, one or more of the lead bodies (e.g., the lead bodies 106 of FIG. 1 or FIG. 2), one or more intermediate devices (e.g., the splitter 207, the lead extension 324 of FIG. 3C, an adaptor, or the like or combinations thereof), or a combination thereof.

Figure 3B:
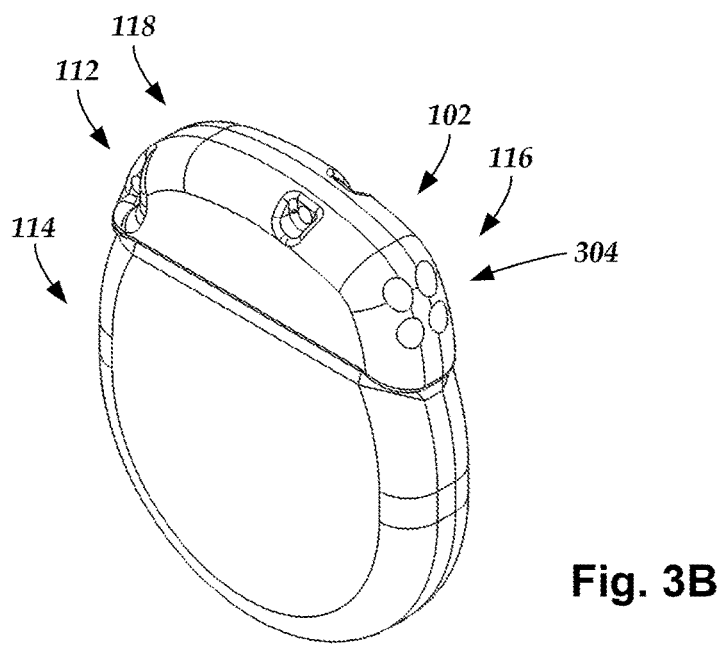
FIG. 3B is a schematic view of another embodiment of the control module of FIG. 1, the control module defining four lead-assembly ports configured for receiving up to four elongated members of one or more lead assemblies, the control module, according to the invention.

The control-module connector 144 defines at least one lead-assembly port 304 into which a proximal end portion of the lead assembly 300 can be inserted, as shown by directional arrows 312a and 312b. In FIG. 3A (and in other figures), the connector housing 112 is shown having two lead-assembly ports 304a and 304b. The connector housing 112 can define any suitable number of lead-assembly ports including, for example, one, two, three, four, five, six, seven, eight, or more lead-assembly ports. FIG. 3B illustrates an alternate embodiment of the control module 102 with four lead-assembly ports 304 disposed in the connector housing 112. The lead-assembly ports 304 shown in each of FIGS. 3A-3B extend from the first end 116 of the connector housing 112.

As shown in FIG. 3A, the control-module connector 144 also includes a plurality of connector contacts, such as connector contact 314, disposed within each lead-assembly port 304a and 304b. When the one or more lead assemblies 300 are inserted into the one or more lead-assembly ports 304a and 304b, the connector contacts 314 can be aligned with terminals 310 disposed along the proximal end portion(s) of the one or more lead assemblies 300 to electrically couple the control module 102 to the electrodes (134 of FIG. 1 or 2). Examples of connectors in control modules are found in, for example, U.S. Pat. Nos. 7,244,150 and 8,224,450, which are incorporated by reference.

Figure 3C:
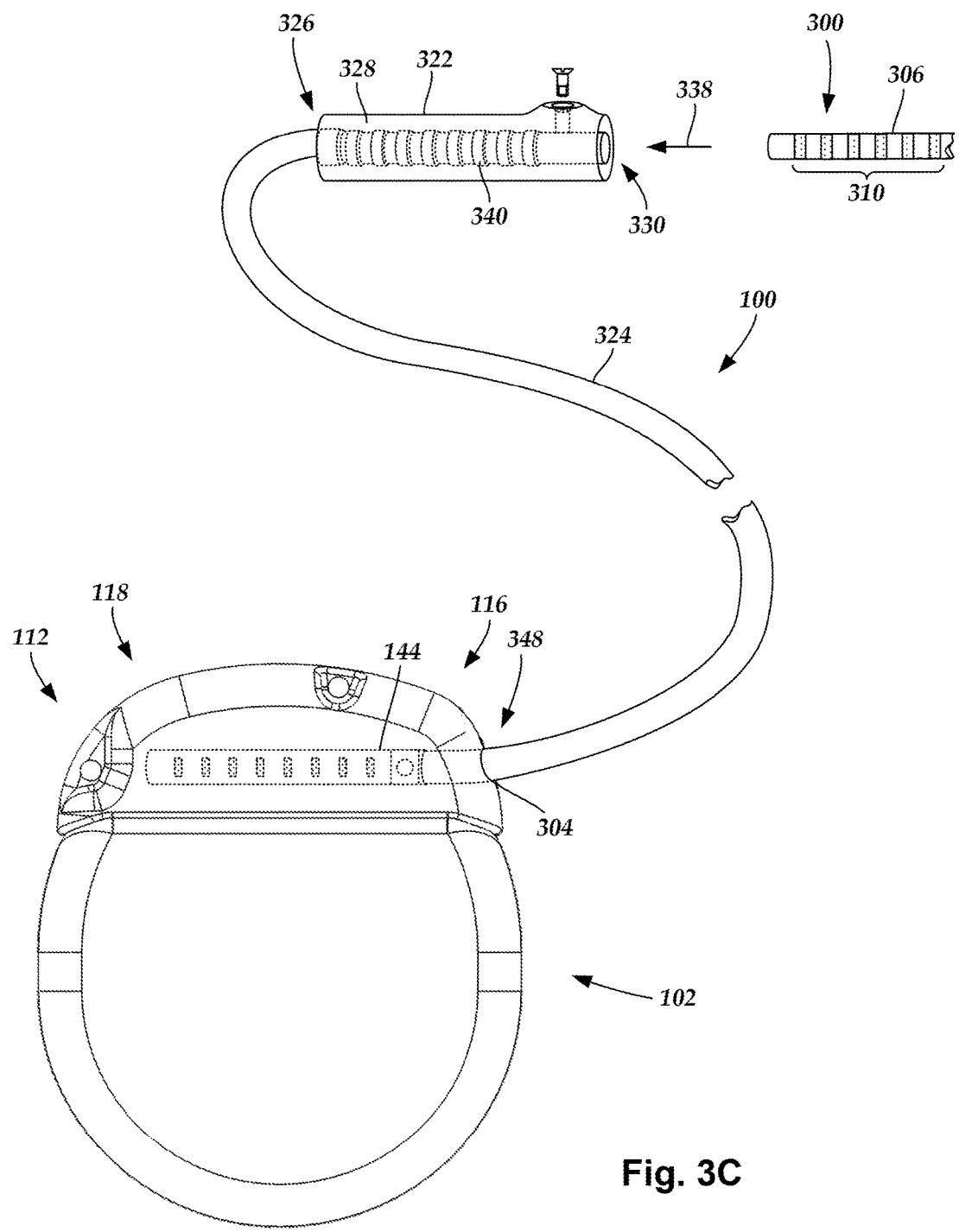
FIG. 3C is a schematic view of one embodiment of an elongated member of the lead assembly of FIG. 3A and a lead extension coupled to the control module of FIG. 1, the lead extension configured to receive the elongated member, according to the invention.

FIG. 3C is a schematic side view of another embodiment of the electrical stimulation system 100. The electrical stimulation system 100 includes a lead extension 324 that is configured and arranged to couple one or more elongated members (e.g., one or more lead bodies, splitters, adaptors, another lead extension, or the like or combinations thereof) of the lead assembly 300 to the control module 102. In FIG. 3B, the lead extension 324 is shown coupled to a single lead-assembly port 304 defined in the control-module connector 144. Additionally, the lead extension 324 is shown configured and arranged to couple to a single elongated member 306. In alternate embodiments, the lead extension 324 is configured and arranged to couple to multiple lead-assembly ports 304 defined in the control-module connector 144, or to receive multiple elongated members, or both.

A lead-extension connector 322 is disposed on the lead extension 324. In FIG. 3B, the lead-extension connector 322 is shown disposed along a distal end portion 326 of the lead extension 324. The lead-extension connector 322 includes a connector housing 328. The connector housing 328 defines at least one lead-assembly port 330 into which terminals 310 of the elongated device can be inserted, as shown by directional arrow 338. The connector housing 328 also includes a plurality of connector contacts, such as connector contact 340. When the elongated device 306 is inserted into the lead-assembly port 330, the connector contacts 240 disposed in the connector housing 328 can be aligned with the terminals 310 of the elongated device to electrically couple the lead extension 324 to the electrodes (134 of FIGS. 1 and 2) disposed along the lead (103 in FIGS. 1 and 2).

In at least some embodiments, a proximal end portion 348 of the lead extension 324 is similarly configured and arranged as a proximal end portion of the lead 103 (or other elongated member 306). The lead extension 324 may include a plurality of conductors that electrically couple the connector contacts 340 to the proximal end portion 348 of the lead extension 324 that is opposite to the distal end portion 326. In at least some embodiments, the conductors disposed in the lead extension 324 can be electrically coupled to a plurality of terminals (not shown) disposed along the proximal end portion 348 of the lead extension 324. In at least some embodiments, the proximal end portion 348 of the lead extension 324 is configured and arranged for insertion into a connector disposed in another lead extension (or another intermediate device). In other embodiments (and as shown in FIG. 3B), the proximal end portion 348 of the lead extension 324 is configured and arranged for insertion into the control-module connector 144.

Figure 4:
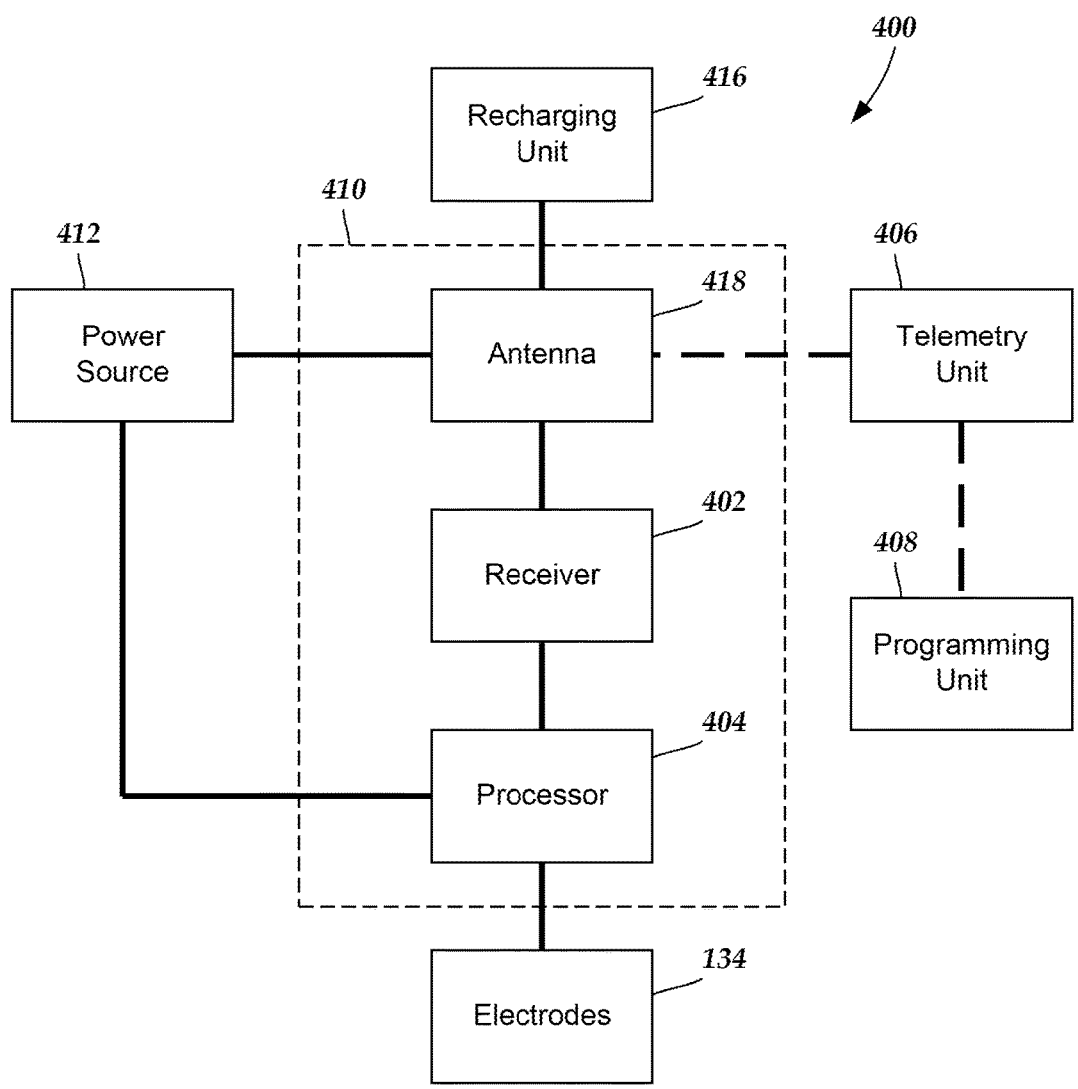
FIG. 4 is schematic overview of one embodiment of components of a stimulation system, including an electronic subassembly disposed within a control module, according to the invention.

FIG. 4 is a schematic overview of one embodiment of components of an electrical stimulation system 400 including an electronic subassembly 410 disposed within a control module. It will be understood that the electrical stimulation system can include more, fewer, or different components and can have a variety of different configurations including those configurations disclosed in the stimulator references cited herein.

Some of the components (for example, a power source 412, an antenna 418, a receiver 402, and a processor 404) of the electrical stimulation system can be positioned on one or more circuit boards or similar carriers within a sealed housing of an implantable pulse generator, if desired. Any power source 412 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 418 or a secondary antenna. The external power source can be in a device that is mounted on the skin of the user or in a unit that is provided near the user on a permanent or periodic basis.

If the power source 412 is a rechargeable battery, the battery may be recharged using the optional antenna 418, if desired. Power can be provided to the battery for recharging by inductively coupling the battery through the antenna to a recharging unit 416 external to the user. Examples of such arrangements can be found in the references identified above.

In one embodiment, electrical stimulation signals are emitted by the electrodes 134 on the paddle or lead body to stimulate nerve fibers, muscle fibers, or other body tissues near the electrical stimulation system. The processor 404 is generally included to control the timing and electrical characteristics of the electrical stimulation system. For example, the processor 404 can, if desired, control one or more of the timing, frequency, strength, duration, and waveform of the pulses. In addition, the processor 404 can select which electrodes can be used to provide stimulation, if desired. In some embodiments, the processor 404 selects which electrode(s) are cathodes and which electrode(s) are anodes. In some embodiments, the processor 404 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 408 that, for example, allows modification of pulse characteristics. In the illustrated embodiment, the processor 404 is coupled to a receiver 402 which, in turn, is coupled to the optional antenna 418. This allows the processor 404 to receive instructions from an external source to, for example, direct the pulse characteristics and the selection of electrodes, if desired.

In one embodiment, the antenna 418 is capable of receiving signals (e.g., RF signals) from an external telemetry unit 406 which is programmed by the programming unit 408. The programming unit 408 can be external to, or part of, the telemetry unit 406. The telemetry unit 406 can be a device that is worn on the skin of the user or can be carried by the user and can have a form similar to a pager, cellular phone, or remote control, if desired. As another alternative, the telemetry unit 406 may not be worn or carried by the user but may only be available at a home station or at a clinician's office. The programming unit 408 can be any unit that can provide information to the telemetry unit 406 for transmission to the electrical stimulation system 400. The programming unit 408 can be part of the telemetry unit 406 or can provide signals or information to the telemetry unit 406 via a wireless or wired connection. One example of a suitable programming unit is a computer operated by the user or clinician to send signals to the telemetry unit 406.

The signals sent to the processor 404 via the antenna 418 and the receiver 402 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 400 to cease operation, to start operation, to start charging the battery, or to stop charging the battery. In other embodiments, the stimulation system does not include the antenna 418 or receiver 402 and the processor 404 operates as programmed.

Optionally, the electrical stimulation system 400 may include a transmitter (not shown) coupled to the processor 404 and the antenna 418 for transmitting signals back to the telemetry unit 406 or another unit capable of receiving the signals. For example, the electrical stimulation system 400 may transmit signals indicating whether the electrical stimulation system 400 is operating properly or not or indicating when the battery needs to be charged or the level of charge remaining in the battery. The processor 404 may also be capable of transmitting information about the pulse characteristics so that a user or clinician can determine or verify the characteristics.

Figure 5:
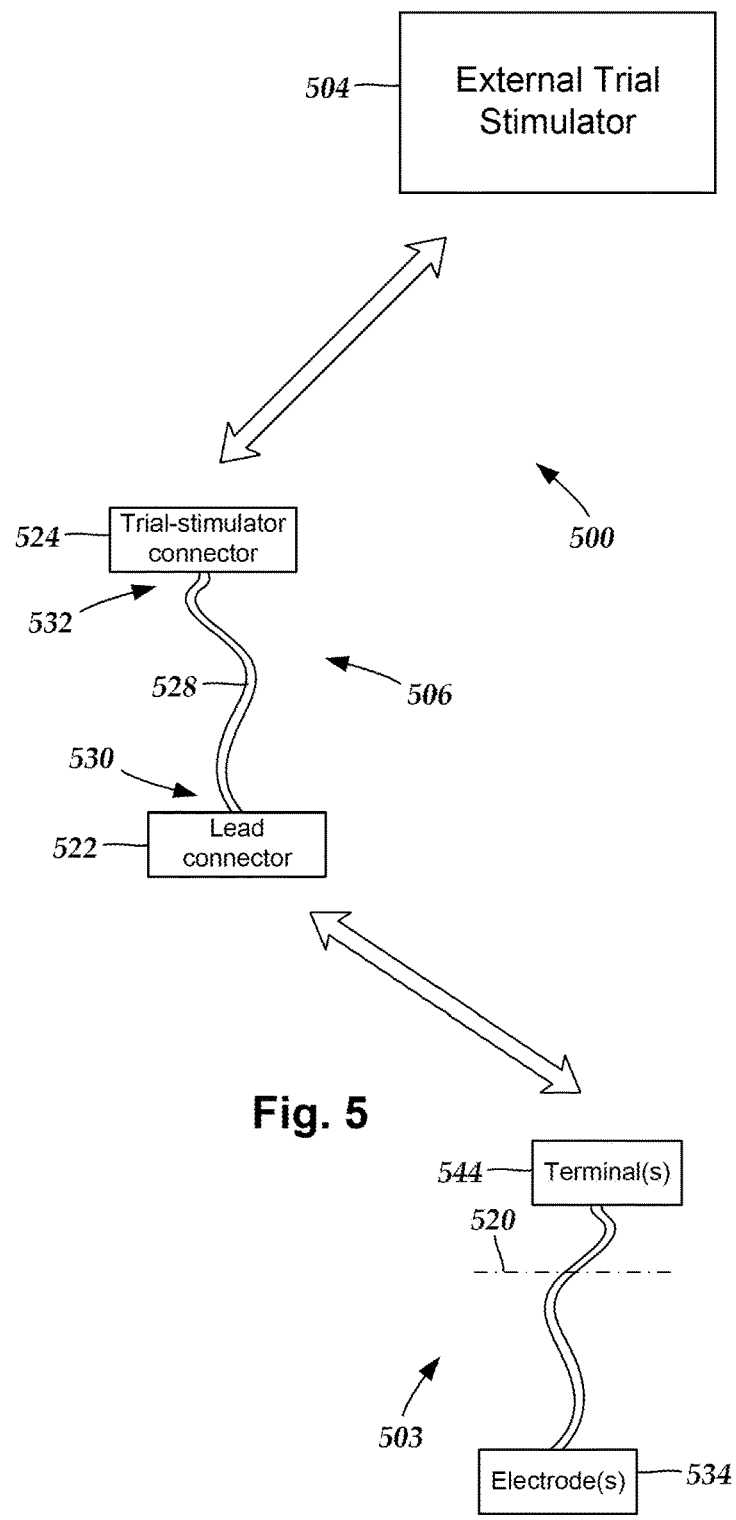
FIG. 5 is a schematic view of one embodiment of a trial stimulation system that includes a lead that is at least partially inserted into a patient and is coupleable to an external trial stimulator, according to the invention.

Turning to FIG. 5, providing therapy using electrical stimulation is typically a long-term process. Consequently, at least some stimulation systems provide stimulation (via one or more implanted leads) to the patient over an extended period of time, such as the operational lifetime of the system, the remaining lifetime of the patient, or at least 1, 5, 10, 15, 20, or more years.

In some instances, the potential efficacy of electrical stimulation for a particular patient is tested prior to implantation of the final lead or control module. One way to test efficacy is to perform a trial stimulation (for example, a trial deep brain or spinal cord stimulation) where an electrode-including distal portion of a lead (and, optionally, one or more lead extensions) is temporarily inserted into the patient. The proximal portion of the lead (or lead extension) can then be electrically coupled to a trial stimulator that is disposed external to the patient to perform trial stimulations using the one or more electrodes. Once efficacy is established, the trial stimulation system can be removed and replaced with another lead and implantable control module (see e.g., FIG. 1 or 2).

The trial stimulations may continue for a short period (e.g., 3-14 days). The testing may include sending the patient home with the trial stimulation system to assess the effectiveness of the therapy to determine if a permanent implanted system will be effective in treating the medical condition. During the trial stimulations, the proximal portion of the lead (or the proximal portion of a lead extension coupled to the lead) can be coupled directly to the trial stimulation. Alternately, the lead can be coupled to the trial stimulator by coupling the proximal portion of the lead (or the proximal portion of a lead extension coupled to the lead) to an operating room cable ("cable") that, in turn, is electrically coupled to the trial stimulator.

FIG. 5 is a schematic view of one embodiment of a trial stimulation system 500 that includes a lead 503, an external trial stimulator 504, and one or more cables 506 that couple the lead 503 to the external trial stimulator 504. The lead 503 includes one or more electrodes 534 and one or more terminals 544. During operation, the electrode(s) 534 are disposed internal to the patient, while the terminal(s) 544 remain external to the patient, as shown in FIG. 5 by a line 520 schematically representing patient skin. In alternate embodiments, the lead may be coupled to a lead extension, where the entire lead and a distal portion of the lead extension are disposed in the patient while lead extension terminals remain external to the patient.

The terminal(s) 512 are configured and arranged to couple the electrode(s) 534 to the external trial stimulator 504. In at least some embodiments, a lead connector 322 of the cable 506 is configured and arranged to couple to the terminal(s) 544 of the lead 503 (or lead extension) and a trial stimulator connector 524 of the cable 506 is configured and arranged to couple to the external trial stimulator 504.

Stimulation therapy can be used to treat a number of diseases, disorders, and conditions including, but not limited to, pain, Parkinson's Disease, Alzheimer's Disease, essential tremor, epilepsy, dystonia, depression, obsessive-compulsive disorder, addiction, Tourette's syndrome, eating disorders (such as anorexia, bulimia, or obesity), other neurological diseases and disorders, or the like. To provide a stimulation therapy, the stimulation parameters for the therapy can be selected using the trial stimulation arrangement illustrated in FIG. 5 or the implantable stimulation arrangements illustrated in FIGS. 1-4 or by any combination thereof. In at least some embodiments, a clinician will vary stimulation parameters and measure the resulting stimulation effects or side effects. For example, a score can be associated with any stimulation effect or side effect associated with the set of stimulation parameters. For example, in a patient afflicted with Parkinson's Disease, the score may be based on any suitable rating scale (for example, the Unified Parkinson's Disease Rating Scale (UPDRS)).

One example of a neurostimulation technique includes providing intermittent bursts of electrical stimulation delivered individually to multiple, spatially separated stimulation field; for example, delivering stimulation using multiple individual electrodes, or multiple groups of electrodes, so that stimulation fields are provided at different locations at different times. These bursts are staggered temporally and spatially relative to each other with different portions of patient tissue (e.g., the brain or spinal cord) stimulated at different times. In at least some embodiments, the bursts are delivered in a specific pattern which repeats in time and can be periodic. In other embodiments, the bursts may be delivered in a quasi-periodic manner. Although the present invention is not bound by any particular theory of operation, it is thought that this type of stimulation, by activating different groups of neurons, in a phase- or time-delayed manner, removes or reduces pathological synchrony between the firing patterns of these neurons. Preclinical, clinical and computational modeling data appears to support the validity of this model. Examples of such methods and techniques can be found in U.S. Pat. Nos. 7,917,221; 7,974,698; 8,000,796; 8,116,874; 8,463,378; and 8,538,547 and U.S. Provisional Patent Application Ser. Nos. 62/053,589 and 62/053,414, all of which are incorporated herein by reference.

Although not wanting to be bound by any particular theory, it is thought that Parkinson's disease and many other neurological and neuropsychiatric disorders may be characterized by pathological synchronization of activity between different neurons. By delivering short bursts of electrical stimulation pulses delivered sequentially to spatially separated electrodes (or groups of electrodes), the neurostimulation technique is directed to disrupting this synchrony and restore more normal firing patterns in the neurons.

Although the present invention is not bound by any particular theory of operation, it has been observed that high amplitudes of neurostimulation therapy (those amplitudes that have been found to be efficacious is previous methods of deep brain stimulation) described above may be less effective than low amplitudes in at least some instances. In particular, preclinical and computational modeling data of deep brain stimulation shows that if such neurostimulation is performed at amplitudes comparable to the efficacious amplitudes for conventional deep brain stimulation, there may be no, or little, symptom reduction, even though emergent symptom reduction is observed over a time-scale of several hours to days. Symptom reduction can be acute if observed during stimulation or sub-acute if observed after a waiting period following stimulation. In contrast, when neurostimulation therapy described above is delivered at an amplitude of about a third of the conventional deep brain stimulation amplitude, an immediate acute or sub-acute symptom reduction is often seen.

The parameter space of this neurostimulation therapy can be rather large. The methods, techniques, and systems described herein present several systematic approaches to exploring such a parameter space to arrive at an efficacious and beneficial set of stimulation parameters. Such methods, techniques, and systems can include changing neurostimulation settings step by step and observing the patient's response. In at least some embodiments, the best stimulation settings lead to acute or sub-acute symptom reduction, as well as emergent responses.

In at least some embodiments, the methods, techniques, and systems described herein explore the neurostimulation amplitude/duty cycle parameter space to identify parameters that cause an acute or sub-acute effect that meets a threshold or is clinically appreciable. If no such amplitude can be found, then the amplitude is fixed to a default or predetermined value (for example, one third of the conventional stimulation amplitude for the site being stimulated, e.g., deep brain or spinal cord stimulation amplitude) and the duty cycle is explored. If on the other hand, the amplitude exploration leads to identification of an appropriate amplitude, the exploration shifts in the duty cycle, with the goal of identifying a duty cycle that enables at least maintenance of therapy from one day to the next. With respect to amplitude, the amplitude can be delivered using a single electrode or can be delivered by two or more electrodes with the amplitude apportioned between the electrodes in any desired apportionment arrangement (for example, in equal or unequal portions for each electrode).

Figure 6:
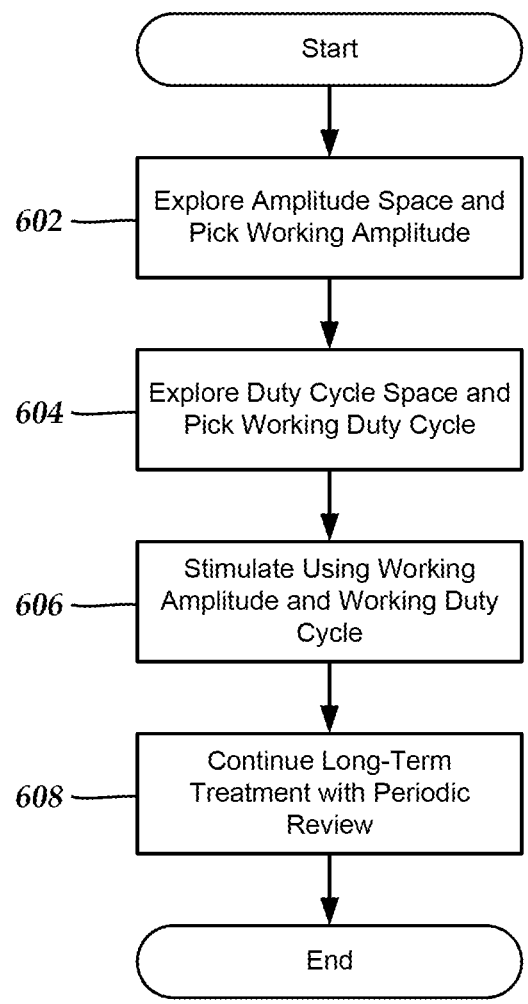
FIG. 6 is a flowchart of one embodiment of a procedure for electrical stimulation of a patient to identify a working amplitude and a working duty cycle, according to the invention.

FIG. 6 is a flowchart of one embodiment of a general procedure for selection of the stimulation amplitude and duty cycle. In step 602, the amplitude space is explored by sequentially stimulating the patient using two or more stimulation amplitudes and observing the response to the stimulation with a resting period between each period of stimulation. A working stimulation amplitude is selected from those used in this process or, in some embodiments, a default stimulation amplitude may also be available for selection. In at least some embodiments, the exploration of the amplitude space may take one day or more or a part of a day (for example, 6, 10, 12, 18 hours or more). In some embodiments, if a working stimulation amplitude is not identified during the initial period of exploration, additional exploration time may be used to test additional stimulation amplitudes. In at least some embodiments, if none of the tested stimulation amplitudes meets one or more threshold criteria, the working stimulation amplitude may be selected to be a predetermined default amplitude. Examples of methods for exploration of the amplitude space are described below in connection with FIGS. 7 and 9. Any suitable threshold criteria can be used and may depend on the observations, effects, or scoring or rating scale used. For example, in some embodiments, such as with Parkinson's Disease, a threshold criterion could be an improvement of 5 points on the UPDRS scale In step 604, the duty cycle space is explored by stimulating the patient using two or more duty cycles and observing the response to the stimulation. A duty cycle (also referred to as a "dosage") can be defined in a number of different ways. For example, the duty cycle can be defined as a daily dosage which indicates the total period of time during which the patient is stimulated such as, for example, 2, 4, 6, 8, 10 or more hours/day. As another example, the duty cycle can be defined as a dosage that is delivered a specified number of times per day such as, for example, 2 hours 2 times/day; 2 hours 4 times/day; 2 hours 6 times/day; 4 hours 2 times/day; or the like. In some embodiments of this example, the number of hours in each delivery can be the same or different and, for embodiments in which the delivery is 3 or more times per day, the period between delivery can be the same or different. It will also be recognized that the delivery period can be specified in hours or minutes or any other unit of time or in terms of total current or power (or any other measurement of the amount of stimulation) delivered. It will also be recognized that the dosage period (one day in the examples above) can be selected to be any suitable period defined in, for example, minutes, days, weeks, months, or the like.

A working duty cycle is selected from those used in this process or, in some embodiments, a default duty cycle may also be available for selection. In at least some embodiments, the exploration of the duty cycle space may take one or more days (for example, one, two, three, four, or five days) or a part of a day (for example, 6, 10, 12, 18 hours or more). In some embodiments, a single duty cycle is tested each day and, for example, the exploration can last 3, 4, 5, or 6 days with a respective number of duty cycles tested. In some embodiments, if a working duty cycle is not identified during the initial period of exploration, additional exploration time may be used to test additional duty cycles. In at least some embodiments, if none of the tested duty cycles meets one or more threshold criteria, the working duty cycle may be selected to be a predetermined default duty cycle. Examples of methods for exploration of the duty cycle space are described below in connection with FIGS. 8 and 10.

Referring back to FIG. 6, in optional step 606, the patient is stimulated using the working stimulation amplitude and the working duty cycle for at least one duty cycle to determine if the stimulation benefits identified in steps 602 and 604 are maintained or remain at or above a threshold level. In some embodiments, the patient is stimulated using the working stimulation amplitude and the working duty cycle for at least one, two, three, four, or more days or cycles. In at least some embodiments, steps 602, 604, and 606 are performed in a hospital, clinic, or other patient care facility. In other embodiments, steps 602 and 604 are performed in a hospital, clinic, or patient care facility and the patient is allowed to return home for step 606 with periodic communication (for example, every one, two, or three days or every 2, 4, 6, 8, or 12 hours) with a clinician. In at least some embodiments, if the stimulation does not maintain the stimulation benefits or remain at or above a threshold level in step 606, then step 602 or step 604 (or both) can be repeated. In other embodiments, if the stimulation does not maintain the stimulation benefits or remain at or above a threshold level in step 606, the working stimulation amplitude or the working duty cycle (or both) can be set to default values.

In step 608, the patient continues to be stimulated using the working stimulation amplitude and working duty cycle for long term treatment with periodic review by the clinician. In some embodiments, the initial in-person review can be, for example, one week, two weeks, one month, or one, two, three, four, five, or six days after the completion of step 606 (or step 604 is step 606 is not performed) although there may be more frequent communication (for example, every 2, 4, 6, 8, 12 hours or every day) via telephone, e-mail, mobile app, or the like with the clinician. Continuing review can be made with the same period or with a longer period. In at least some embodiments, if the stimulation benefits are not maintained or do not remain at or above a threshold level, the procedure of FIG. 6 can be repeated. In other embodiments, if the stimulation benefits are not maintained or do not remain at or above a threshold level, a clinician, patient, or other user may adjust the stimulation amplitude or duty cycle or both (or any other stimulation parameter.)

In at least some embodiments where a trial lead is used to perform the procedure of FIG. 6, when a satisfactory result is obtained and maintained for a period of time (for example, one, two, three, or four week or one month), the patient may return for implantation of a permanent lead and electrical stimulation system. In at least some embodiments, the steps of FIG. 6 (or a subset of those steps) may be performed after implantation of the permanent lead to confirm or adjust the stimulation parameters (such as stimulation amplitude or duty cycle).

In some embodiments of the procedure, step 602 is performed on a first day, step 604 is performed for several days (for example, two, three, four, or five days), step 606 is performed for several days (for example, two, three, four, or five days), and step 608 is performed for several days or weeks (for example, three, four, five, six, or ten days or one, two, three, or four weeks.).

Figure 7:
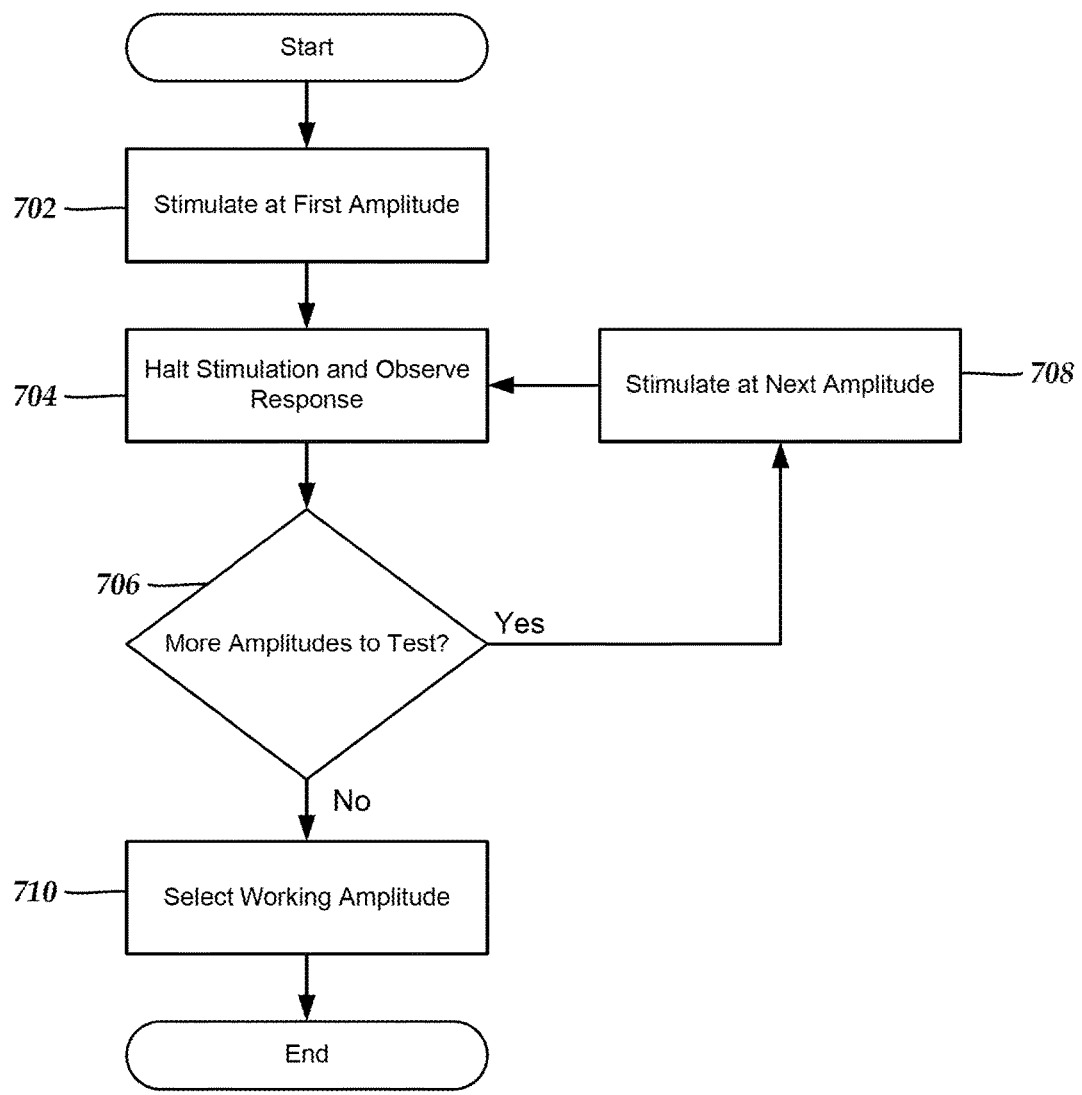
FIG. 7 is a flowchart of another embodiment of a procedure for electrical stimulation of a patient to identify a working amplitude, according to the invention.

FIG. 7 is a flowchart of one embodiment of a method for exploring the amplitude space. In step 702, a first stimulation amplitude is selected and the patient is stimulated using the first stimulation amplitude for a test period of time. In at least some embodiments, some or all patient medications may be halted or reduced prior to (for example, 1, 2, 4 or more hours before or the night before or the day before) the stimulation. For example, patient medications relevant to the disease or disorder to be treated may be halted or reduced. Alternatively or additionally, patient medications that may mask or affect the expected stimulation effects or stimulation side effects may be halted or reduced. In at least some embodiments, if the patient is receiving electrical stimulation prior to step 702, the stimulation may be halted or reduced at least 1, 2, 4, 10, 12, 24, or more hours prior to step 702.

Any suitable first stimulation amplitude can be selected. For example, the first stimulation amplitude can be a fraction (for example, one half, one third, one quarter, or one fifth) of a typical stimulation amplitude for the site being stimulated, e.g., deep brain or spinal cord stimulation amplitude. The typical stimulation amplitude may depend on the disease or disorder being treated, on the implantation site, on the brain or spinal cord structure being targeted, on the disease progression, on patient demographics, on the electrode combination used, or the like or any combination thereof. Examples of typical deep brain stimulation amplitudes include, but are not limited to 2, 3, 4, 5, or 6 mA. Examples of a first stimulation amplitude include, but are not limited to, 0.5, 1, 1.5, 2, 2.5, 3, 3.5, 4, 4.5, 5, 5.5, or 6 mA. In some embodiments, several stimulation amplitudes are identified for testing and one of the amplitudes is selected. Such selection can be random, by lowest amplitude, by highest amplitude, or by any other selection criteria.

The test period for the first stimulation amplitude (or for any other stimulation amplitude that is to be tested) can be any suitable value including, but not limited to, one, two, three, four, six, twelve, or more hours or 10, 15, 30, 45, 90, or more minutes. In at least some embodiments, a clinician may select a test period based on factors such as, for example, expected time to observe stimulation effect or stimulation side effect, expected dosage period, the disease or disorder being treated, patient demographics, the body structure (e.g., brain or spinal cord structure) being stimulated, the disease progression, or the like, or any combination thereof. In at least some embodiments, the clinician or patient may terminate the delivery of the first stimulation amplitude at any time during the test period for reasons including, but not limited to, patient discomfort, lack of sufficient therapy, or the like, or any combination thereof.

In step 704, the stimulation is halted and the response to the stimulation is observed by the clinician, patient, others, or any combination thereof. In at least some embodiments, the stimulation response may be observed immediately after cessation of stimulation. In some embodiments, the stimulation response may be observed after a waiting period (for example, 2, 5, 10, 15, 30, 45, 60 minutes or more) after cessation of stimulation. There may be multiple observations after different waiting periods. In some embodiments, the stimulation response may be observed during stimulation. In some embodiments, any combination of these observations (during stimulation, immediately after stimulation, or after one or more waiting period) can be used.

The observation of the stimulation response can take any suitable form including, but not limited to, patient or clinician verbal or written comments about the response; a rating (for example, in the case of Parkinson's Disease, the UPDRS score or any other suitable scale) by the clinician, patient, or others or any combination thereof; measurements or tests by internal or external sensors (such as wearable or implanted devices); or the like or any combination thereof. In some embodiments, the observation may be directed to one or more specific stimulation effects, stimulation side effects, or any combination thereof.

In step 706, it is determined whether there are more amplitudes to test. In some embodiments, several amplitudes are identified for testing prior to the start of testing. In some embodiments, a clinician may decide to test another amplitude based on the outcome of previous testing. If there are more amplitudes to test, then the process proceeds to step 708; if not, the process proceeds to step 710.

In step 708, another amplitude is selected and the patient is stimulated using the new amplitude and then the process proceeds to step 704. Any method of selection of the next amplitude for testing can be used. For example, such selection can be random, by lowest untested amplitude, by highest untested amplitude, or by any other selection criteria. In at least some embodiments, a period of waiting time, after the preceding stimulation, may be instituted before stimulating with the newly selected amplitude. Any suitable waiting time can be used including, but not limited to, 5, 10, 15, 30, 45, 60, 90, 120 minutes or longer. In at least some embodiments, the waiting time between each stimulation is the same or nearly the same (for example, within 5%, 10%, 20%, or 25%).

The sequence of steps 708, 704, 706 can be repeated for every stimulation amplitude to be tested. When all of the desired stimulation amplitudes have been tested (or when the clinician or patient decides to terminate testing or any other reason for termination of testing) a working amplitude can be selected (step 710).

Any selection criteria can be used. For example, the tested amplitude with the best score may be selected. In some embodiments, the lowest amplitude which meets or exceeds a desired score threshold may be selected. In some embodiments (for example, those where the amplitude in a list are randomly tested), a working amplitude is selected based on a difference between the score for that amplitude and a preceding (or succeeding) amplitude. In some embodiments, amplitudes which have significant side effects (for example, meet or exceed a threshold side effect score) may be rejected and a non-rejected amplitude selected on any other criteria (including those described above). In some embodiments, if no tested amplitude meets a threshold criterion for efficacy (or if the clinician or patient feels that no tested amplitude is adequate or better than another) a default amplitude may be selected. For example, the default amplitude may be the typical stimulation amplitude for the site being stimulated, e.g., deep brain or spinal cord stimulation amplitude, discussed above or some fraction of the amplitude (for example, one half or one third). The working amplitude can then be used in the exploration of the duty cycle.

Figure 8:
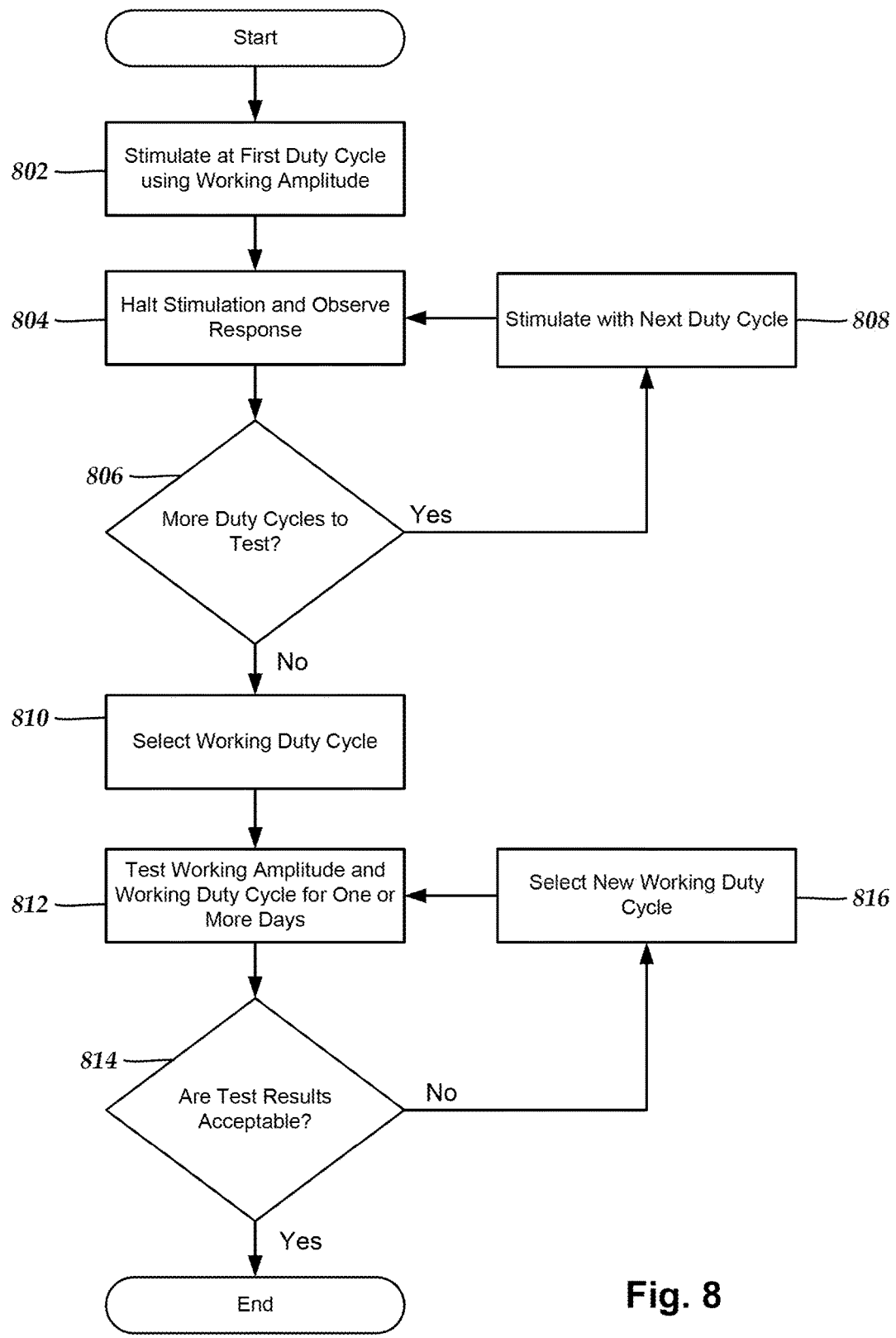
FIG. 8 is a flowchart of a further embodiment of a procedure for electrical stimulation of a patient to identify a working duty cycle, according to the invention.

FIG. 8 is a flowchart of one embodiment of a method for exploring the duty cycle space using the working amplitude (or some other selected amplitude). In step 802, a first duty cycle is selected and the patient is stimulated using the working stimulation amplitude and the first duty cycle for a test period of time. In at least some embodiments, some or all patient medications may be halted or reduced prior to (for example, 1, 2, 4 or more hours before or the night before or the day before) the stimulation. For example, patient medications relevant to the disease or disorder to be treated may be halted or reduced. Alternatively or additionally, patient medications that may mask or affect the expected stimulation effects or stimulation side-effects may be halted or reduced. In at least some embodiments, if the patient is receiving electrical stimulation prior to step 802, the stimulation may be halted or reduced at least 1, 2, 4, 10, 12, 24, or more hours prior to step 802.

Any suitable first stimulation duty cycle can be selected. The duty cycle can be defined in a variety of manners as described above with respect to step 604 of FIG. 6. For illustrative purposes, a duty cycle specifying a stimulation period and a number of stimulation periods per day will be used, but it will be understood that any other method of defining a duty cycle can be used for the methods described herein. For example, the first duty cycle can be 2 hours 2×/day (two times per day), 2 hours 4×/day, 2 hours 6×/day, 4 hours 2×/day, or the like. Such selection of the first duty cycle can be random, by shortest total stimulation time, by longest total stimulation time, or by any other selection criteria.

The test period for the first duty cycle (or for any other duty cycle that is to be tested) can be any suitable value including, but not limited to, 12 hours, 18 hours, one day, two days, or more. In at least some embodiments, a clinician may select a test period based on factors such as, for example, expected time to observer stimulation effect or stimulation side effect, expected dosage period, the disease or disorder being treated, patient demographics, the body structure (e.g., brain or spinal cord structure) being stimulated, the disease progression, or the like, or any combination thereof. In at least some embodiments, the clinician or patient may terminate the delivery of stimulation at any time during the test period for reasons including, but not limited to, patient discomfort, ineffectiveness, side-effects, or the like, or any combination thereof.

In step 804, the response to the stimulation is observed by the clinician, patient, others, or any combination thereof and at the end of the test period the stimulation is halted. Because the duty cycle testing is typically over a longer period than the amplitude testing, observation of response will often occur during the test period. For example, observation of response may occur during or after each (or at least one or every other) period of stimulation in the duty cycle. In at least some embodiments, the stimulation response may be observed immediately after cessation of stimulation. In some embodiments, the stimulation response may be observed after a waiting period (for example, 2, 5, 10, 15, 30, 45, 60 minutes or more) after cessation of stimulation. There may be multiple observations after different waiting periods. In some embodiments, the stimulation response may be observed during stimulation. In some embodiments, any combination of these observations (during stimulation, immediately after stimulation, or after one or more waiting period) can be used.

The observation of the stimulation response can take any suitable form including, but not limited to, patient or clinician verbal or written comments about the response; a rating (for example, in the case of Parkinson's Disease, the UPDRS score or any other suitable scale) by the clinician, patient, or others or any combination thereof; measurements or tests by internal or external sensors (such as wearable or implanted devices); or the like or any combination thereof. In some embodiments, the observation may be directed to one or more specific stimulation effects, stimulation side effects, or any combination thereof.

In step 806, it is determined whether there are more duty cycles to test. In some embodiments, several duty cycles are identified for testing prior to the start of testing. In some embodiments, a clinician may decide to test another duty cycle based on the outcome of previous testing. If there are more duty cycles to test, then the process proceeds to step 808; if not, the process proceeds to step 810.

In step 808, another duty cycle is selected and the patient is stimulated using the working amplitude and the new duty cycle and then the process proceeds to step 804. Any method of selection of the next duty cycle for testing can be used. For example, such selection can be random, by shortest total stimulation time of untested duty cycles, by longest stimulation time of untested duty cycles, or by any other selection criteria. In at least some embodiments, a period of waiting time, after the preceding stimulation, may be instituted before stimulating with the newly selected duty cycle. Any suitable waiting time can be used including, but not limited to, 30 minutes, 1 hours, 1½ hours, 2 hours, 3 hours, hours, or longer. In at least some embodiments, the waiting time between each stimulation is the same or nearly the same (for example, within 5%, 10%, 20%, or 25%).

The sequence of steps 808, 804, 806 can be repeated for every stimulation duty cycle to be tested. When all of the desired duty cycles have been tested (or when the clinician or patient decides to terminate testing or any other reason for termination of testing) a working duty cycle can be selected (step 810).

Any selection criteria can be used. For example, the tested duty cycle with the best score may be selected. In some embodiments, the duty cycle with the lowest dosage which meets or exceeds a desired score threshold may be selected. In some embodiments (for example, those where the duty cycle in a list are randomly tested), a working duty cycle is selected based on a difference between the score for that duty cycle and a preceding (or succeeding) duty cycle. In some embodiments, duty cycles which have significant side effects (for example, meet or exceed a threshold side effect score) may be rejected and a non-rejected duty cycle selected on any other criteria (including those described above). In some embodiments, if no tested duty cycle meets a threshold criterion for efficacy (or if the clinician or patient feels that no tested duty cycle is adequate or better than another) a default duty cycle may be selected. For example, the default duty cycle may be 4 stimulations for 2 hours each; 2 stimulations for 4 hours each; or 2 stimulations for 2 hours each.

Optional steps 812-816 are used to determine if the working amplitude and working duty cycle maintain efficacy in stimulation (or result in side effects) when applied over one or more days. In step 812, the patient is stimulated for one or more days using the working amplitude and the working duty cycle. During or after this time, the response to the stimulation can be observed. For example, observation of response may occur during or after each (or at least one or every other) period of stimulation in the duty cycle. In at least some embodiments, the stimulation response may be observed immediately after cessation of stimulation. In some embodiments, the stimulation response may be observed after a waiting period (for example, 1, 2, 4, 6, 12, hours or more or 1, 2, 3 days or more) after cessation of stimulation. There may be multiple observations after different waiting periods. In some embodiments, the stimulation response may be observed during stimulation. In some embodiments, any combination of these observations (during stimulation, immediately after stimulation, or after one or more waiting period) can be used. The observation can use the same testing or scoring methods described above with respect to step 804 or different methods or criteria can be used.

In step 814, it is determined whether the results of the testing in step 812 are acceptable. In some embodiments, the results of the testing are acceptable if the results are at or above a threshold score criteria or if the results maintain the scores observed for the working amplitude and working duty cycle in step 804. In other embodiments, the results of the testing are acceptable if the results are at or above a projected or extrapolated score based on the cores observed for the working amplitude and working duty cycle in step 804. In some embodiments, the results of the testing may be unacceptable if side effects are observed or meet or exceed a threshold criterion.

In some embodiments, if the results of testing are acceptable a longer term of testing (see step 608 above) may be started. In some embodiments, if the results of the testing are acceptable a long term lead or implantable pulse generator may be implanted in the patient for long term stimulation. In some embodiments, if the results of the testing are not acceptable, a new working duty cycle (or new working amplitude or both) may be selected (step 816) and tested (step 812). In some embodiments, if the results of the testing are not acceptable, a default duty cycle (or default amplitude or both) may be selected for long term stimulation.

In some embodiments, the steps 812-816 can be performed in two separate phases. In a first phase, the steps 812-816 are performed at a hospital or other patient care facility for a period of time (for example, two, three, four, five, six, or seven days or longer) with relative frequent observation (for example, after every stimulation period or every 2, 4, 6, 8, 12 hours or more). In a second phase, the steps 812-816 are repeated and performed at the patient's home or other care facility for a period of time (for example, five, six, seven, or ten days or 2 weeks or longer) with less frequent observation (for example, one, two, three, or four times per day). In this second phase, the patient or care provider may report observations to the clinician by phone, through e-mail or a software application, or any other method. In at least some embodiments, the clinician can interrupt this second phase if the benefits are not maintained at a desired level or if side effects appear or become too pronounced.

Figure 9:
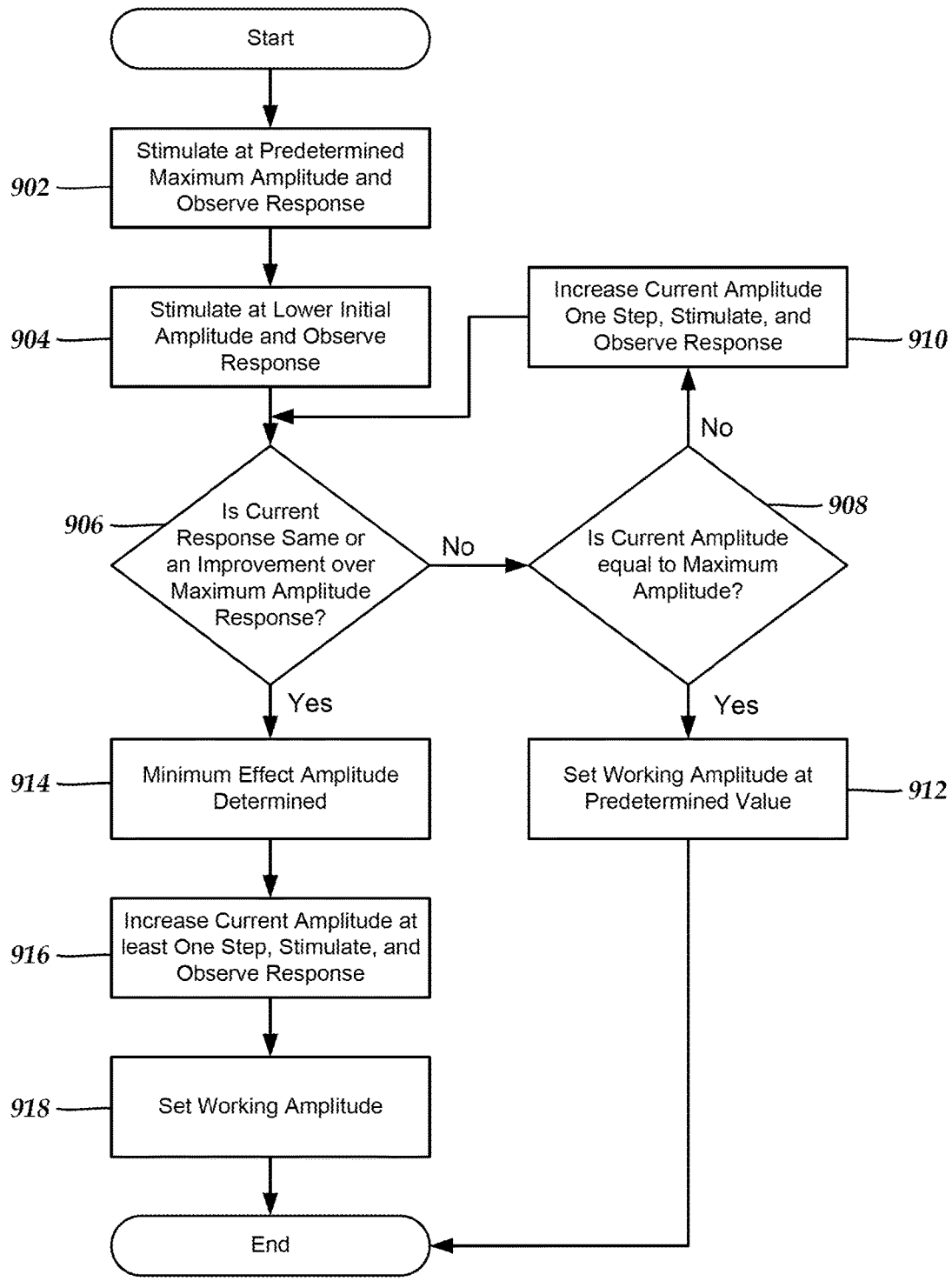
FIG. 9 is a flowchart of yet another embodiment of a procedure for electrical stimulation of a patient to identify a working amplitude, according to the invention.

FIG. 9 is a flowchart of one embodiment of a method for exploring the amplitude space. In step 902, a maximum stimulation amplitude is selected and the patient is stimulated using the maximum stimulation amplitude for a test period of time. In at least some embodiments, some or all patient medications may be halted or reduced prior to (for example, 1, 2, 4 or more hours before or the night before or the day before) the stimulation. For example, patient medications relevant to the disease or disorder to be treated may be halted or reduced. Alternatively or additionally, patient medications that may mask or affect the expected stimulation effects or stimulation side-effects may be halted or reduced. In at least some embodiments, if the patient is receiving electrical stimulation prior to step 902, the stimulation may be halted or reduced at least 1, 2, 4, 10, 12, 24, or more hours prior to step 902.

Any suitable maximum stimulation amplitude can be selected. For example, the maximum stimulation amplitude can be a typical stimulation amplitude for the site being stimulated, e.g., deep brain or spinal cord stimulation amplitude, (as described above for step 702) or a fraction (for example, one half, one third, one quarter, or one fifth) of the typical stimulation amplitude for the site being stimulated, e.g., deep brain or spinal cord stimulation amplitude. The test period for the maximum stimulation amplitude (or for any other stimulation amplitude that is to be tested) can be any suitable value including, but not limited to, one, two, three, four, six, twelve, or more hours or 10, 15, 30, 45, 90, or more minutes. In at least some embodiments, a clinician may select a test period based on factors such as, for example, expected time to observe stimulation effect or stimulation side effect, expected dosage period, the disease or disorder being treated, patient demographics, the body structure (e.g., brain or spinal cord structure) being stimulated, the disease progression, or the like, or any combination thereof. In at least some embodiments, the clinician or patient may terminate the delivery of the maximum stimulation amplitude at any time during the test period for reasons including, but not limited to, patient discomfort, ineffectiveness, side-effects, or the like, or any combination thereof.

The stimulation is halted and the response to the stimulation is observed by the clinician, patient, others, or any combination thereof. In at least some embodiments, the stimulation response may be observed immediately after cessation of stimulation. In some embodiments, the stimulation response may be observed after a waiting period (for example, 2, 5, 10, 15, 30, 45, 60 minutes or more) after cessation of stimulation. There may be multiple observations after different waiting periods. In some embodiments, the stimulation response may be observed during stimulation. In some embodiments, any combination of these observations (during stimulation, immediately after stimulation, or after one or more waiting period) can be used.

The observation of the stimulation response can take any suitable form including, but not limited to, patient or clinician verbal or written comments about the response; a rating (for example, the UPDRS score or any other suitable scale) by the clinician, patient, or others or any combination thereof; measurements or tests by internal or external sensors (such as wearable or implanted devices); or the like or any combination thereof. In some embodiments, the observation may be directed to one or more specific stimulation effects, stimulation side effects, or any combination thereof.

In step 904, stimulation is repeated with a lower initial amplitude. This can be, for example, the lowest amplitude that the clinician intends to explore. The stimulation proceeds for a period of time, as in step 902, and the results are observed in the same manner as for step 902

In step 906, it is determined whether the response for the current stimulation amplitude is the same or an improvement over the response observed for the maximum amplitude in step 902. If not, then the process moves to step 908; if so, then the process moves to step 914.

In step 908, it is determined whether the current stimulation amplitude is the maximum amplitude. If not, then the process moves to step 910; if so, then the process moves to step 912.

In step 910, the current stimulation amplitude is increased one step and stimulation is repeated with the new current stimulation amplitude. The stimulation proceeds for a period of time, as in step 902, and the results are observed in the same manner as for step 902. The procedure of steps 906-910 will continue incrementing the amplitude each cycle until the determinations in either steps 906 or 908 are positive or the clinician or patient terminates the procedure.

In step 912, the working amplitude is set to a default amplitude because none of the tested amplitudes provided the same or improved response relative to the maximum amplitude. In at least some embodiments, the default amplitude is the typical stimulation amplitude for the site being stimulated, e.g., deep brain or spinal cord stimulation amplitude, (as described above for step 702) or a fraction (for example, one half, one third, one quarter, or one fifth) of the typical stimulation amplitude.

In step 914, the current stimulation amplitude from step 906 is set as the minimum effect amplitude. In step 916, the current stimulation amplitude is increased one step (unless the current stimulation amplitude is already the maximum amplitude) and stimulation is repeated with the new current stimulation amplitude. The stimulation proceeds for a period of time, as in step 902, and the results are observed in the same manner as for step 902.

In Step 918, if the response to the current stimulation amplitude is better than the response to the minimum effect amplitude then the working amplitude is set equal to the current stimulation amplitude; if not, set the working amplitude is set equal to the minimum effect amplitude. The working amplitude can then be used in the exploration of the duty cycle.

Figure 10:
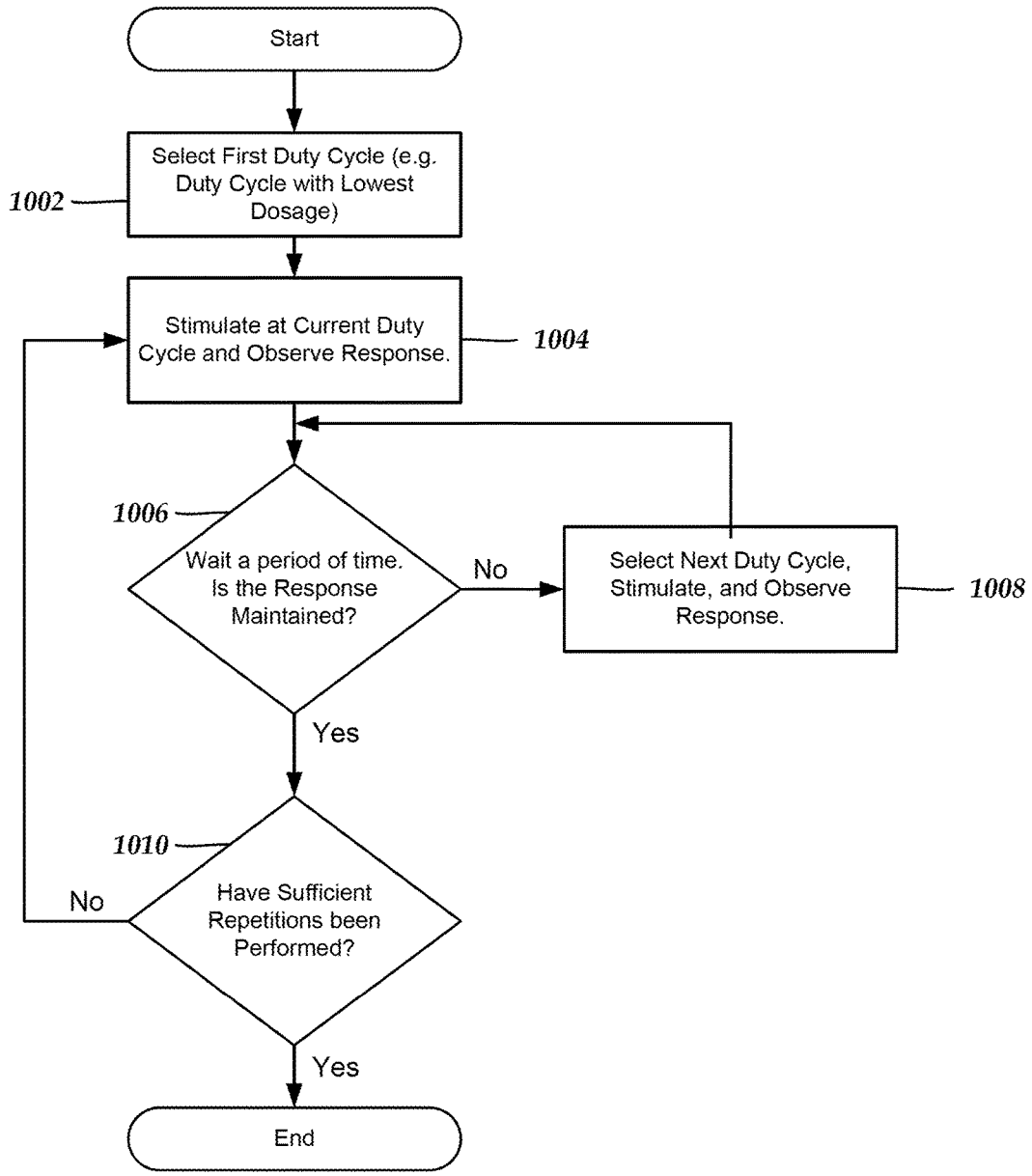
FIG. 10 is a flowchart of a further embodiment of a procedure for electrical stimulation of a patient to identify a working duty cycle, according to the invention.

FIG. 10 is a flowchart of one embodiment of a method for exploring the duty cycle space using the working amplitude (or some other selected amplitude). In step 1002, a first duty cycle is selected and the patient is stimulated using the working stimulation amplitude and the first duty cycle for a test period of time. In at least some embodiments, some or all patient medications may be halted or reduced prior to (for example, 1, 2, 4 or more hours before or the night before or the day before) the stimulation. For example, patient medications relevant to the disease or disorder to be treated may be halted or reduced. Alternatively or additionally, patient medications that may mask or affect the expected stimulation effects or stimulation side-effects may be halted or reduced. In at least some embodiments, if the patient is receiving electrical stimulation prior to step 1002, the stimulation may be halted or reduced at least 1, 2, 4, 10, 12, 24, or more hours prior to step 1002.

Any suitable first duty cycle can be selected. The duty cycle can be defined in a variety of manners as described above with respect to step 604 of FIG. 6. For illustrative purposes, a duty cycle specifying a stimulation period and a number of stimulation periods per day will be used, but it will be understood that any other method of defining a duty cycle can be used for the methods described herein. For example, the first duty cycle can be 2 hours 2×/day (two times per day), 2 hours 4×/day, 2 hours 6×/day, 4 hours 2×/day, or the like. In one embodiment, the first duty cycle selected is the duty cycle with the lowest dosage (i.e., the duty cycle with the shortest total stimulation time).

In step 1004, the patient is stimulated using the first duty cycle and the response to the stimulation is observed by the clinician, patient, others, or any combination thereof and at the end of the test period the stimulation is halted. The test period for the first duty cycle (or for any other duty cycle that is to be tested) can be any suitable value including, but not limited to, 12 hours, 18 hours, one day, two days, or more. In at least some embodiments, a clinician may select a test period based on factors such as, for example, expected time to observer stimulation effect or stimulation side effect, expected dosage period, the disease or disorder being treated, patient demographics, the body structure (e.g., brain or spinal cord structure) being stimulated, the disease progression, or the like, or any combination thereof. In at least some embodiments, the clinician or patient may terminate the delivery of stimulation at any time during the test period for reasons including, but not limited to, patient discomfort, ineffectiveness, side-effects, or the like, or any combination thereof.

Because the duty cycle testing is typically over a longer period than the amplitude testing, observation of response will often occur during the test period. For example, observation of response may occur during or after each (or at least one or every other) period of stimulation in the duty cycle. In at least some embodiments, the stimulation response may be observed immediately after cessation of stimulation. In some embodiments, the stimulation response may be observed after a waiting period (for example, 2, 5, 10, 15, 30, 45, 60 minutes or more) after cessation of stimulation. There may be multiple observations after different waiting periods. In some embodiments, the stimulation response may be observed during stimulation. In some embodiments, any combination of these observations (during stimulation, immediately after stimulation, or after one or more waiting period) can be used.

The observation of the stimulation response can take any suitable form including, but not limited to, patient or clinician verbal or written comments about the response; a rating (for example, the UPDRS score or any other suitable scale) by the clinician, patient, or others or any combination thereof; measurements or tests by internal or external sensors (such as wearable or implanted devices); or the like or any combination thereof. In some embodiments, the observation may be directed to one or more specific stimulation effects, stimulation side effects, or any combination thereof.

In step 1006, there is a waiting period of time, for example, waiting until the next day, and then it is determined whether the response from the first stimulation at the current duty cycle is maintained. If not, the process moves to step 1008; if so, the process moves to step 1010.

In step 1008, the duty cycle is increased to the next dosage and the patient is stimulated using the new duty cycle and the response is observed. The process then moves to step 1006. The cycle of steps 1006, 1008 is repeated with incrementally increasing the duty cycle dosage until the desired response is maintained.

In step 1010, it is determined if sufficient repetitions of stimulation at the current duty cycle have been performed. In some embodiments, the current duty cycle is performed two, three, four, or five or more times to ensure that the response is maintained over a longer period of time than a single duty cycle. If sufficient repetitions have not been performed, the process moves to step 1004; otherwise, the process ends.

In some embodiments, the testing is continued at the patient's home or other care facility for a period of time (for example, five, six, seven, or ten days or 2 weeks or longer) with less frequent observation (for example, one, two, three, or four times per day). The patient or care provider may report observations to the clinician by phone, through e-mail or a software application, or any other method. In at least some embodiments, the clinician can interrupt this second phase if the benefits are not maintained at a desired level or if side effects appear or become too pronounced.

In addition to exploring the amplitude/duty cycle parameter space, it may be useful to varying other stimulation parameters. This may be particularly useful in situations where a suitable or desired response has not been obtained during the exploration of the amplitude or duty cycle (or both amplitude and duty cycle) parameter space. Alternatively, a clinician may choose to vary a third stimulation parameter to determine whether the patient response can be improved or side effects can be reduced or power consumption can be reduced or for any other reason.

In at least some embodiments, the stimulation is provided by a series of bursts of stimulation pulses. Such stimulation has, as stimulation parameters, the pulse frequency (i.e., the frequency of pulses within a burst) and the burst frequency (i.e., the repeat frequency of the bursts). The burst frequency is an example of one stimulation parameter than can be varied in a manner similar to the amplitude and duty cycle parameters described above. In at least some embodiments, the burst frequency is in the range of 1 to 100 Hz or in the range of 2 to 50 Hz or in the range of 5 to 30 Hz. Other stimulation parameters, such as the pulse frequency, can be used in the methods described below in place of the burst frequency.

Figure 11:
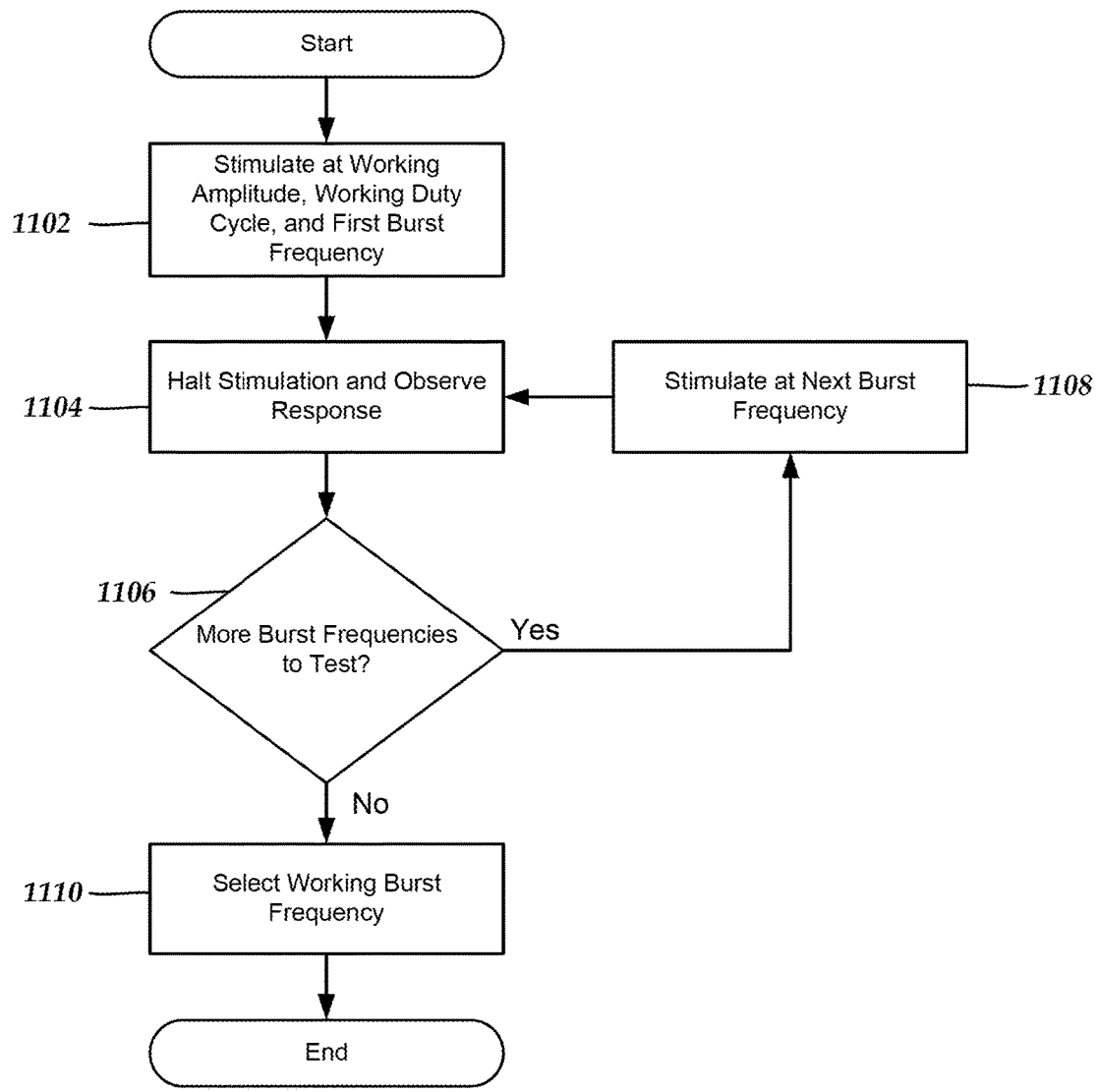
FIG. 11 is a flowchart of an embodiment of a procedure for electrical stimulation of a patient to identify a working burst frequency, according to the invention.

FIG. 11 is a flowchart of one embodiment of a method for exploring the burst frequency space. This method could be added to any of the methods illustrated in FIGS. 7-10. For example, the method could be added at a point where a working amplitude and working duty cycle have been selected. Alternatively, the method could be modified, by removal of references to a working duty cycle in the description below, and used after a working amplitude is selected.

In step 1102, a first burst frequency is selected and the patient is stimulated using the first burst frequency, a working amplitude, and a working duty cycle (such as a working amplitude and working duty cycle identified in any of the methods described above with reference to FIGS. 11-10) for a test period of time. In at least some embodiments, some or all patient medications may be halted or reduced prior to (for example, 1, 2, 4 or more hours before or the night before or the day before) the stimulation. For example, patient medications relevant to the disease or disorder to be treated may be halted or reduced. Alternatively or additionally, patient medications that may mask or affect the expected stimulation effects or stimulation side effects may be halted or reduced. In at least some embodiments, if the patient is receiving electrical stimulation prior to step 1102, the stimulation may be halted or reduced at least 1, 2, 4, 10, 12, 24, or more hours prior to step 1102.

Any suitable first burst frequency can be selected. For example, the first burst frequency can be in the range of 1 to 100 Hz or in the range of 2 to 50 Hz or in the range of 5 to 30 Hz. A first burst frequency may depend on the disease or disorder being treated, on the implantation site, on the brain or spinal cord structure being targeted, on the disease progression, on patient demographics, on the electrode combination used, or the like or any combination thereof. Examples of a first burst frequency include, but are not limited to, 5, 10, 15, 20, 25, 30, 40, or 50 Hz. In some embodiments, several burst frequencies are identified for testing and one of the burst frequencies is selected. Such selection can be random, by lowest burst frequency, by highest burst frequency, or by any other selection criteria.

The test period for the first burst frequency (or for any other burst frequency that is to be tested) can be any suitable value any of the test periods described above with respect to the methods illustrated in FIGS. 7-10. In at least some embodiments, a clinician may select a test period based on factors such as, for example, expected time to observe stimulation effect or stimulation side effect, the disease or disorder being treated, patient demographics, the body structure (e.g., brain or spinal cord structure) being stimulated, the disease progression, or the like, or any combination thereof. In at least some embodiments, the clinician or patient may terminate the delivery of the stimulation at any time during the test period for reasons including, but not limited to, patient discomfort, lack of sufficient therapy, ineffectiveness, side-effects, or the like, or any combination thereof.

In step 1104, the stimulation is halted and the response to the stimulation is observed by the clinician, patient, others, or any combination thereof. In at least some embodiments, the stimulation response may be observed immediately after cessation of stimulation. In some embodiments, the stimulation response may be observed after a waiting period (for example, any of the waiting periods described above with respect to the methods illustrated in FIGS. 7-10) after cessation of stimulation. There may be multiple observations after different waiting periods. In some embodiments, the stimulation response may be observed during stimulation. In some embodiments, any combination of these observations (during stimulation, immediately after stimulation, or after one or more waiting period) can be used.

The observation of the stimulation response can take any suitable form including, but not limited to, patient or clinician verbal or written comments about the response; a rating (for example, in the case of Parkinson's Disease, the UPDRS score or any other suitable scale) by the clinician, patient, or others or any combination thereof; measurements or tests by internal or external sensors (such as wearable or implanted devices); or the like or any combination thereof. In some embodiments, the observation may be directed to one or more specific stimulation effects, stimulation side effects, or any combination thereof.

In step 1106, it is determined whether there are more burst frequencies to test. In some embodiments, several burst frequencies are identified for testing prior to the start of testing. In some embodiments, a clinician may decide to test another burst frequency based on the outcome of previous testing. If there are more burst frequencies to test, then the process proceeds to step 1108; if not, the process proceeds to step 1110.

In step 1108, another burst frequency is selected and the patient is stimulated using the new burst frequency and then the process proceeds to step 1104. Any method of selection of the next burst frequency for testing can be used. For example, such selection can be random, by lowest untested burst frequency, by highest untested burst frequency, or by any other selection criteria. In at least some embodiments, a period of waiting time, after the preceding stimulation, may be instituted before stimulating with the newly selected burst frequency. Any suitable waiting time can be used including, but not limited to, the waiting times described above with respect to the methods illustrated in FIGS. 7-10. In at least some embodiments, the waiting time between each stimulation is the same or nearly the same (for example, within 5%, 10%, 20%, or 25%).

The sequence of steps 1108, 1104, 1106 can be repeated for every burst frequency to be tested. When all of the desired burst frequencies have been tested (or when the clinician or patient decides to terminate testing or any other reason for termination of testing) a working burst frequency can be selected (step 1110).

Any selection criteria can be used. For example, the tested burst frequency with the best score may be selected. In some embodiments, the lowest burst frequency which meets or exceeds a desired score threshold may be selected. In some embodiments (for example, those where the burst frequency in a list are randomly tested), a working burst frequency is selected based on a difference between the score for that burst frequency and a preceding (or succeeding) burst frequency. In some embodiments, burst frequencies which have significant side effects (for example, meet or exceed a threshold side effect score) may be rejected and a non-rejected burst frequency selected on any other criteria (including those described above). In some embodiments, if no tested burst frequency meets a threshold criterion for efficacy (or if the clinician or patient feels that no tested burst frequency is adequate or better than another) a default burst frequency may be selected.

In some embodiments, one or more other stimulation parameters may be substituted for amplitude, duty cycle, or burst frequency in any of the methods described herein. Such stimulation parameters can include, for example, burst duration, pulse frequency, or the like.

In some embodiments, the total stimulation amplitude may be delivered by more than one electrode with each electrode delivering a portion of the stimulation amplitude. Changing the portion of the stimulation amplitude delivered by each of multiple electrodes can be called "current steering." It may be desirable to test different apportionments of the total stimulation amplitude among multiple electrodes. A procedure to determine a working apportionment of the total stimulation amplitude similar to that described above for burst frequency, in conjunction with FIG. 11, can be used to test different apportionments of the total stimulation amplitude among multiple electrodes. The apportionments may be defined, for example, in values (e.g., a number of mA) of amplitude or in percentages of the total stimulation amplitude. This procedure may be performed in addition to, or as a substitute for, the procedure used to determine a working burst frequency or working duty cycle or working amplitude.

For example, in at least some embodiments, a method can includes stimulating the patient using the electrical stimulation lead and the working amplitude, working duty cycle, or working burst frequency (or any combination thereof) at different current steering settings (i.e., different apportionments of the total stimulation amplitude among two or more electrodes); selecting a working combination of current steering settings based on the responses from the tested current steering settings and, optionally, a default current steering setting; and stimulating the patient using the electrical stimulation lead, the working amplitude, the working duty cycle, the working burst frequency, and the working current steering settings (or any combination thereof).

It will be understood that the system can include one or more of the methods described hereinabove with respect to FIGS. 6-11 in any combination. The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. The methods described herein can be performed using any type of processor (including any type of microprocessor) or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks or described for systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A method for electrical stimulation of a patient, the method comprising:

a) implanting at least a portion of an electrical stimulation lead comprising a plurality of electrodes disposed along a distal end portion of the electrical stimulation lead;
b) stimulating the patient using the electrical stimulation lead at a plurality of test stimulation amplitudes;
c) observing a response for each of the plurality of test stimulation amplitudes;
d) selecting a working stimulation amplitude based on the responses from a group consisting of the plurality of test stimulation amplitudes and, optionally, a default stimulation amplitude;
e) stimulating the patient using the electrical stimulation lead and the working amplitude at a plurality of test duty cycles, wherein each of the test duty cycles is defined as either 1) a daily dosage which indicates a total amount of stimulation time, stimulation current, or stimulation power delivered to the patient in one day or 2) a combination of i) a dosage which indicates an amount of stimulation time, stimulation current, or stimulation power delivered to the patient per dosage and ii) a number of times per day the dosage is administered;
f) observing a response for each of the plurality of test duty cycles;
g) selecting a working duty cycle based on the responses from a group consisting of the plurality of test duty cycles and, optionally, a default duty cycle; and
h) stimulating the patient using the electrical stimulation lead, the working amplitude, and the working duty cycle.

2. The method of claim 1, further comprising
i) stimulating the patient using the electrical stimulation lead and the working amplitude and working duty cycle at a plurality of test burst frequencies, wherein each of the burst frequencies corresponds to a repeat frequency of bursts of pulses, wherein a pulse frequency is a frequency of pulses within the burst;
j) observing a response for each of the plurality of test burst frequencies;
k) selecting a working burst frequency based on the responses from a group consisting of the plurality of test burst frequencies and, optionally, a default burst frequency; and
l) stimulating the patient using the electrical stimulation lead, the working amplitude, and the working burst frequency.

3. The method of claim 1, wherein stimulating the patient using the electrical stimulation lead at a plurality of test stimulation amplitudes comprises randomly selecting an order of the test stimulation amplitudes.

4. The method of claim 1, wherein stimulating the patient using the electrical stimulation lead and the working amplitude at a plurality of test duty cycles comprises randomly selecting an order of the test duty cycles.

5. The method of claim 1, wherein observing a response for each of the plurality of test stimulation amplitudes comprises scoring a response for each of the plurality of test stimulation amplitudes.

6. The method of claim 1, wherein observing a response for each of the plurality of test duty cycles comprises scoring a response for each of the plurality of test duty cycles.

7. The method of claim 1, further comprising i) after stimulating the patient using the electrical stimulation lead, the working amplitude, and the working duty cycle, observing a response for the stimulation; and j) determining whether the response for the stimulation maintains a threshold level of response.

8. The method of claim 7, wherein determining whether the response for the stimulation maintains a threshold level of response comprises determining whether the response for the stimulation maintains a threshold level of response for each of at least two successive days.

9. The method of claim 7, wherein steps a) to j) are performed at a hospital or patient care facility and then step i) is repeated at a patient home and then step j) is repeated with a clinician.

10. The method of claim 7, wherein steps b) to d) are performed on a first day, steps e) to g) are performed over a course of a plurality of second days following the first day, and steps h) to j) are performed over a course of a plurality of third days following the plurality of second days.

11. The method of claim 1, wherein selecting a working stimulation amplitude comprises selecting the default stimulation amplitude if responses for the test stimulation amplitudes fail to meet a threshold criterion.

12. A system for electrical stimulation of a patient, the system comprises
an implantable electrical stimulation lead comprising a plurality of electrodes disposed along a distal end portion of the electrical stimulation lead; and
a computer processor configured and arranged to perform the following actions:
   a) stimulate a patient using the electrical stimulation lead at a plurality of test stimulation amplitudes;
   b) receive a response for each of the plurality of test stimulation amplitudes;
   c) select a working stimulation amplitude based on the responses from a group consisting of the plurality of test stimulation amplitudes and, optionally, a default stimulation amplitude;
   d) stimulate the patient using the electrical stimulation lead and the working amplitude at a plurality of test duty cycles, wherein each of the test duty cycles is defined as either 1) a daily dosage which indicates a total amount of stimulation time, stimulation current, or stimulation power delivered to the patient in one day or 2) a combination of i) a dosage which indicates an amount of stimulation time, stimulation current, or stimulation power delivered to the patient per dosage and ii) a number of times per day, week, or month the dosage is administered;
   e) receive a response for each of the plurality of test duty cycles;
   f) select a working duty cycle based on the responses from a group consisting of the plurality of test duty cycles and, optionally, a default duty cycle; and
   g) stimulate the patient using the electrical stimulation lead, the working amplitude, and the working duty cycle.

13. The system of claim 12, further comprising a trial stimulator coupleable to the implantable electrical stimulation lead and configured and arranged to provide stimulation through the electrical stimulation lead.

14. The system of claim 12, further comprising an implantable control module coupleable to the implantable electrical stimulation lead and configured and arranged to provide stimulation through the electrical stimulation lead.

15. The system of claim 12, wherein stimulate the patient using the electrical stimulation lead at a plurality of test stimulation amplitudes comprises randomly select an order of the test stimulation amplitudes.

16. The system of claim 12, wherein stimulate the patient using the electrical stimulation lead at a plurality of test duty cycles comprises randomly select an order of the test duty cycles.

17. The system of claim 12, wherein receive a response for each of the plurality of test stimulation amplitudes comprises receive a score of a response for each of the plurality of test stimulation amplitudes.

18. A non-transitory computer-readable storage medium having processor-executable instructions for identifying a set of stimulation parameters, the processor-executable instructions when installed onto a device enable the device to perform actions, including:
   a) stimulate a patient using the electrical stimulation lead at a plurality of test stimulation amplitudes;
   b) receive a response for each of the plurality of test stimulation amplitudes;
   c) select a working stimulation amplitude based on the responses from a group consisting of the plurality of test stimulation amplitudes and, optionally, a default stimulation amplitude;
   d) stimulate the patient using the electrical stimulation lead and the working amplitude at a plurality of test duty cycles, wherein each of the test duty cycles is defined as either 1) a daily dosage which indicates a total amount of stimulation time, stimulation current, or stimulation power delivered to the patient in one day or 2) a combination of i) a dosage which indicates an amount of stimulation time, stimulation current, or stimulation power delivered to the patient per dosage and ii) a number of times per day the dosage is administered;
   e) receive a response for each of the plurality of test duty cycles;
   f) select a working duty cycle based on the responses from a group consisting of the plurality of test duty cycles and, optionally, a default duty cycle; and
   g) stimulate the patient using the electrical stimulation lead, the working amplitude, and the working duty cycle.

19. The non-transitory computer-readable storage medium of claim 18, wherein receive a response for each of the plurality of test stimulation amplitudes comprises receive a score of a response for each of the plurality of test stimulation amplitudes.

20. The non-transitory computer-readable storage medium of claim 18, wherein receive a response for each of the plurality of test duty cycles comprises receive a score of a response for each of the plurality of test duty cycles.

* * * * *